(12) United States Patent
Jackson et al.

(10) Patent No.: US 11,562,818 B2
(45) Date of Patent: Jan. 24, 2023

(54) SYSTEM FOR EXTENDED REALITY VISUAL CONTRIBUTIONS

(71) Applicant: AT&T Intellectual Property I, L.P., Atlanta, GA (US)

(72) Inventors: James Jackson, Austin, TX (US); Eric Zavesky, Austin, TX (US); James Pratt, Round Rock, TX (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 254 days.

(21) Appl. No.: 16/891,161

(22) Filed: Jun. 3, 2020

(65) Prior Publication Data

US 2021/0383912 A1 Dec. 9, 2021

(51) Int. Cl.
*G16H 20/70* (2018.01)
*A61B 5/16* (2006.01)
(Continued)

(52) U.S. Cl.
CPC ............. *G16H 20/70* (2018.01); *A61B 5/165* (2013.01); *G06T 19/006* (2013.01); *G09B 9/00* (2013.01)

(58) Field of Classification Search
CPC ...... G16H 20/70; A61B 5/165; G06T 19/006; G09B 9/00; B60T 7/18; B60T 7/22; B60T 17/18; B60T 2210/32; A61M 21/0094; A61M 2021/0022; A61M 2021/0027; A61M 2021/005; A61M 2205/3317; A61M 2205/332; A61M 2205/3368; A61M 2205/3375; A61M 2205/3553; A61M 2205/3592; A61M 2205/80; A61M 2205/8237; A61M 2230/30; A61M 21/02; A61M 2205/505; A61M 2205/507; A61M 2205/52; A61M 2205/609; A61M 2205/8206; A61M 2205/8262; A61M 2209/088; A61M 2230/06;
(Continued)

(56) References Cited

U.S. PATENT DOCUMENTS

2021/0343085 A1* 11/2021 Chakravarthi ......... G06V 20/20

OTHER PUBLICATIONS

Kanamori et al., Obstacle Avoidance Method in Real Space for Virtual Reality Immersion, Oct. 2018, In 2018 IEEE International Symposium on Mixed and Augmented Reality (ISMAR), pp. 80-89. (Year: 2018).*

(Continued)

*Primary Examiner* — Jeffery A Brier
(74) *Attorney, Agent, or Firm* — Guntin & Gust, PLC; John G. Rauch

(57) ABSTRACT

Aspects of the subject disclosure may include, for example, receiving information about a task to be completed by a user, receiving information about the user and receiving information about a physical environment of the user. The subject disclosure may further include creating one or more immersion objects based on the information about the task, the information about the user and the information about the physical environment, creating an immersive environment including the one or more immersive objects and at least a portion of the physical environment of the user, and communicating to an extended reality (XR) device of the user information about the immersive environment to create an immersive experience for completion of the task by the user. Other embodiments are disclosed.

20 Claims, 8 Drawing Sheets

(51) Int. Cl.
    *G06T 19/00*        (2011.01)
    *G09B 9/00*         (2006.01)
(58) Field of Classification Search
    CPC .......... A61M 2230/42; A61M 2230/62; A61M
                   2230/63; A61M 2230/65; A61M 21/00;
                                G06F 2203/011; G06F 3/011
    See application file for complete search history.

(56) References Cited

OTHER PUBLICATIONS

Steptoe et al., Presence and Discernability in Conventional and Non-Photorealistic Immersive Augmented Reality, Sep. 2014, In 2014 IEEE International Symposium on Mixed and Augmented Reality (ISMAR) 2014, pp. 213-218. (Year: 2014).*

Baus et al., Moving from virtual reality exposure-based therapy to augmented reality exposure-based therapy: a review, Mar. 2014, Frontiers in human neuroscience, vol. 8, Article 112, pp. 1-15. (Year: 2014).*

* cited by examiner

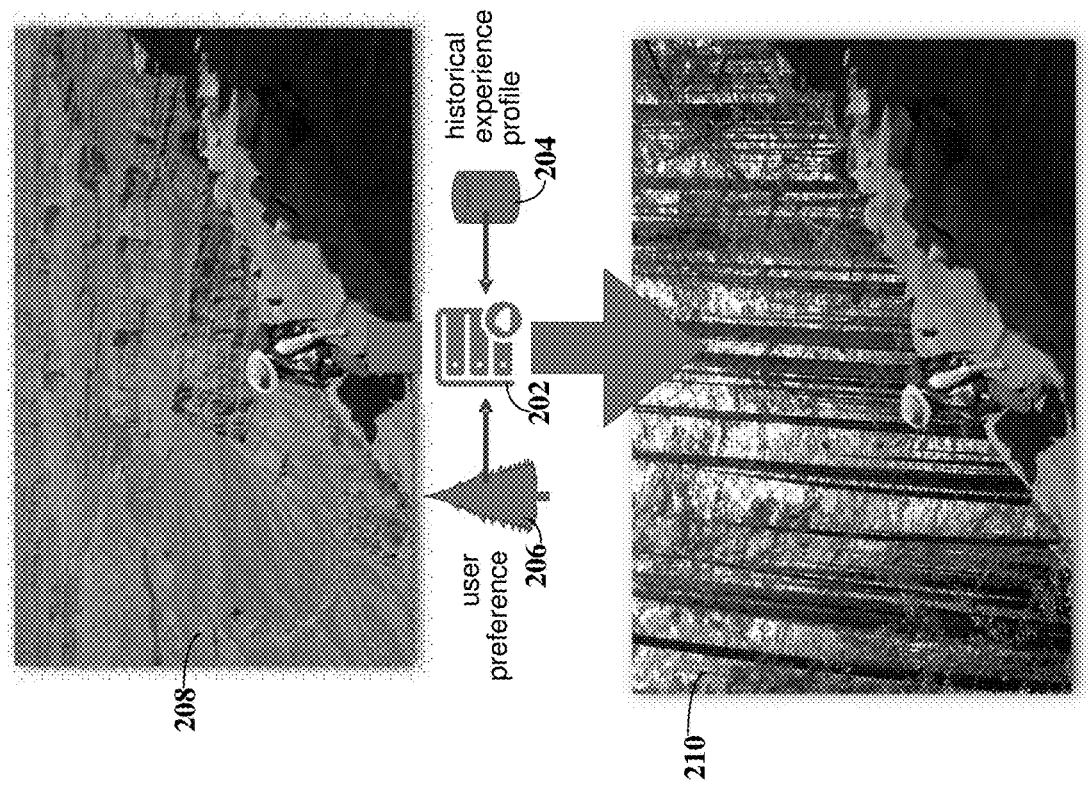

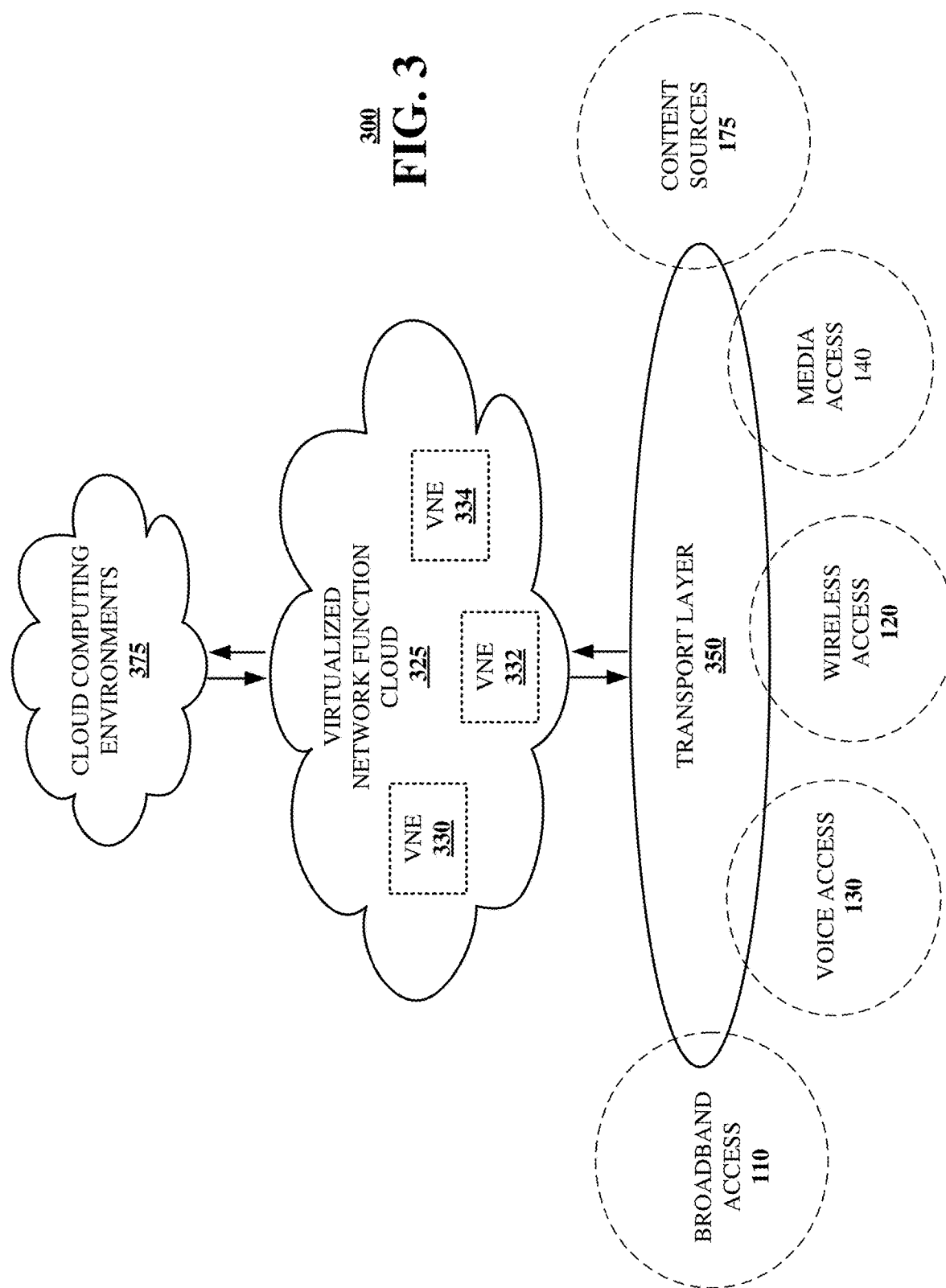

SYSTEM FOR EXTENDED REALITY VISUAL CONTRIBUTIONS

FIELD OF THE DISCLOSURE

The subject disclosure relates to a system and method for extended reality (XR) visual contributions.

BACKGROUND

Immersive technology allows a user to experience a virtual environment or an environment that includes both physical elements and virtual elements.

BRIEF DESCRIPTION OF THE DRAWINGS

Reference will now be made to the accompanying drawings, which are not necessarily drawn to scale, and wherein:

FIG. 2A is a block diagram illustrating an example, non-limiting embodiment of a system functioning within the communication network of FIG. 1 in accordance with various aspects described herein.

FIG. 3 is a block diagram illustrating an example, non-limiting embodiment of a virtualized communication network in accordance with various aspects described herein.

DETAILED DESCRIPTION

Figure 1:
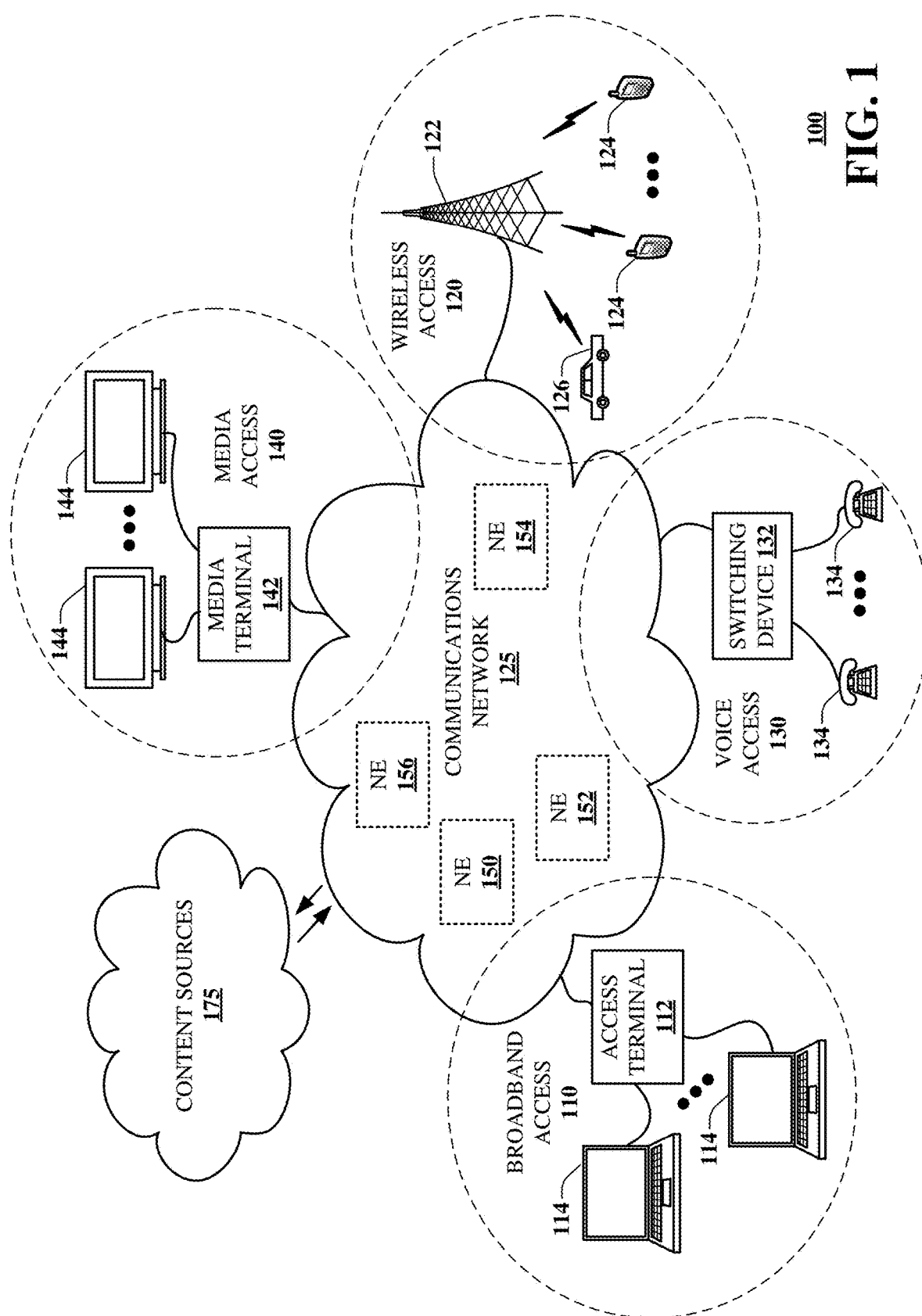
FIG. 1 is a block diagram illustrating an exemplary, non-limiting embodiment of a communications network in accordance with various aspects described herein.

The subject disclosure describes, among other things, illustrative embodiments for synthesizing augmented reality experiences for users, taking various inputs into consideration. Exemplary inputs may include user preferences and historic information about the user and an environment, as well as what objects and items are currently present in the environment of the user. The user may have certain preferences and interests that may drive the synthesis. Other inputs include tasks the user may be trying to complete. The subject disclosure describes method and apparatus which can augment the environment presented to a user in a way to facilitate the completion of tasks by the user or to enable other engagement with an environment by the user. Functionally, the system facilitates manipulating images that might be displayed by an augmented reality system and applying that capability to various use cases. The system and method enable modification of a presented display or experience to a user. The input information about the user and user preferences may come from the widest variety of sources including user-configurable information, information learned about the user including historical information and including information developed by machine learning and artificial intelligence sources, as well as social media accounts of the user and others, and other sources as well. Decisions derived from machine learning or artificial intelligence may be based on data from the user, or on data from similar users, or on aggregate data from many users, for example. Other embodiments are described in the subject disclosure.

One or more aspects of the subject disclosure include receiving information about a task to be completed by a user, receiving information about the user and receiving information about a physical environment of the user. The subject disclosure may further include creating one or more immersion objects based on the information about the task, the information about the user and the information about the physical environment, creating an immersive environment including the one or more immersive objects and at least a portion of the physical environment of the user, and communicating to an extended reality (XR) device of the user information about the immersive environment to create an immersive experience for completion of the task by the user.

One or more aspects of the subject disclosure include receiving information about training to be completed by a user, information about a physical environment of the user, including information about a training object associated with the training to be completed by the user and creating one or more immersion objects. The creating may be based on the information about the training to be completed by the user and the information about the physical environment. The subject disclosure may further include creating an immersive environment including the one or more immersive objects and at least a portion of the physical environment of the user, adjusting an image of the immersive environment to focus attention of the user on the training object and communicating, to an extended reality (XR) device of the user, information about the immersive environment to create an immersive experience for completion of the training by the user.

One or more aspects of the subject disclosure include receiving information about a behavioral modification to be completed by a user, information about the user and information about a physical environment of the user. The subject disclosure may further include creating one or more immersion objects based on the information about the behavioral modification, the information about the user and the information about the physical environment. The subject disclosure may further include creating an immersive environment including the one or more immersive objects and at least a portion of the physical environment of the user and communicating, to an extended reality (XR) device of the user, information about the immersive environment to create an immersive experience for completion of the behavioral modification by the user. The subject disclosure may further include receiving user mood information about a mood of the user during completion of the behavioral modification by the user, modifying the immersive environment based on the mood of the user, and communicating, to the XR device of the user, information about the modified immersive environment.

Referring now to FIG. 1, a block diagram is shown illustrating an example, non-limiting embodiment of a system 100 in accordance with various aspects described herein. For example, system 100 can facilitate in whole or in part providing an immersive environment for a user that includes at least some virtual objects. The mood of the user may be monitored and objects may be modified to adjust the mood of the user. This can be done, for example, the train the user or modify the user's behavior in certain situations. In particular, a communications network 125 is presented for providing broadband access 110 to a plurality of data terminals 114 via access terminal 112, wireless access 120 to a plurality of mobile devices 124 and vehicle 126 via base station or access point 122, voice access 130 to a plurality of telephony devices 134, via switching device 132 and/or media access 140 to a plurality of audio/video display devices 144 via media terminal 142. In addition, communication network 125 is coupled to one or more content sources 175 of audio, video, graphics, text and/or other media. While broadband access 110, wireless access 120, voice access 130 and media access 140 are shown separately, one or more of these forms of access can be combined to provide multiple access services to a single client device (e.g., mobile devices 124 can receive media content via media terminal 142, data terminal 114 can be provided voice access via switching device 132, and so on).

The communications network 125 includes a plurality of network elements (NE) 150, 152, 154, 156, etc. for facilitating the broadband access 110, wireless access 120, voice access 130, media access 140 and/or the distribution of content from content sources 175. The communications network 125 can include a circuit switched or packet switched network, a voice over Internet protocol (VoIP) network, Internet protocol (IP) network, a cable network, a passive or active optical network, a 4G, 5G, or higher generation wireless access network, WIMAX network, UltraWideband network, personal area network or other wireless access network, a broadcast satellite network and/or other communications network.

In various embodiments, the access terminal 112 can include a digital subscriber line access multiplexer (DSLAM), cable modem termination system (CMTS), optical line terminal (OLT) and/or other access terminal. The data terminals 114 can include personal computers, laptop computers, netbook computers, tablets or other computing devices along with digital subscriber line (DSL) modems, data over coax service interface specification (DOCSIS) modems or other cable modems, a wireless modem such as a 4G, 5G, or higher generation modem, an optical modem and/or other access devices.

In various embodiments, the base station or access point 122 can include a 4G, 5G, or higher generation base station, an access point that operates via an 802.11 standard such as 802.11n, 802.11ac or other wireless access terminal. The mobile devices 124 can include mobile phones, e-readers, tablets, phablets, wireless modems, and/or other mobile computing devices.

In various embodiments, the switching device 132 can include a private branch exchange or central office switch, a media services gateway, VoIP gateway or other gateway device and/or other switching device. The telephony devices 134 can include traditional telephones (with or without a terminal adapter), VoIP telephones and/or other telephony devices.

In various embodiments, the media terminal 142 can include a cable head-end or other TV head-end, a satellite receiver, gateway or other media terminal 142. The display devices 144 can include televisions with or without a set top box, personal computers and/or other display devices.

In various embodiments, the content sources 175 include broadcast television and radio sources, video on demand platforms and streaming video and audio services platforms, one or more content data networks, data servers, web servers and other content servers, and/or other sources of media.

In various embodiments, the communications network 125 can include wired, optical and/or wireless links and the network elements 150, 152, 154, 156, etc. can include service switching points, signal transfer points, service control points, network gateways, media distribution hubs, servers, firewalls, routers, edge devices, switches and other network nodes for routing and controlling communications traffic over wired, optical and wireless links as part of the Internet and other public networks as well as one or more private networks, for managing subscriber access, for billing and network management and for supporting other network functions.

FIG. 2A is a block diagram illustrating an example, non-limiting embodiment of a system 200 functioning within the communication network of FIG. 1 in accordance with various aspects described herein. The system 200 may be used as part of a system for extended reality visual contributions. The system 200 in the exemplary embodiment of FIG. 2A includes an augmented reality (AR) system 202, a historical user experience profile 204 and a user preference profile 206. The system 200 may be useful to transform an experience in a particular environment of a user using immersive technology.

Immersive technology allows creation of an immersive experience for a user. An immersive experience is an environment that is, at least in part, illusory and that seems to partially or completely surround the user so that the user feels to be inside the immersive experience and to be a part of the immersive experience. An immersive environment allows the user to experience some things that are physically impossible. An immersive experience may have the effect of augmenting reality or the real world by combining real world features, or supplementing them or replacing them, with artificially created features.

Immersive technology includes equipment such as headsets, AR smart glasses, audio speaker systems and computer control to create immersive experiences. Immersive technology more generally may include other wearable technology, such as gloves, a belt, using additional mechanisms such as haptic feedback. For example, augmented reality (AR) systems use technology such as an AR headset and the camera and screen on a smartphone or tablet to add a computer-simulated layer of information on top of real world features. AR technology is an enhancement of the world surrounding the user. Virtual reality (VR) goes a step further and immerses the uses in a wholly artificial world, a digital simulation and creation with which the user can interact. A VR system will seek to stimulate as many user senses as possible to immerse the user in the simulated environment. Extended reality (XR) refers to environments that combine real and virtual environments and permit human and machine interactions. An XR environment may be generated by computer equipment and be may implemented by wearable technology such as a headset or AR glasses. XR technology may be considered to incorporate AR, VR and other technologies for immersive experiences. As used herein, an immersive environment, an immersive experience, an XR environment, and a scene generally refer to a combination of real and virtual environments for a user under automatic machine control.

As immersive technology is more ubiquitous, there is an opportunity to provide supportive visuals and interaction objects depending on user tasks. For example, by detecting a task or operation of the user, the immersive technology may be employed to supplement or assist in performance of that task. Such support may include display to the user of particular immersive experiences during performance of the task, or substitution by an immersive feature for a real-world experience, again, to supplement or assist in performance of the task. One drawback is that the impact of adding these virtual objects to the user environment may be that the virtual objects may be user-specific or task-specific so they must be appropriately scheduled. Similarly, the selection of which item to create for a user (e.g. crutches, a safety wall, or grass-covered sidewalk) may not be appropriate or effective in all situations.

These problems can be remedied with attention to the user environment, both real and virtual, and a tempered contribution of objects to assist and improve user performance, particularly in an immersive environment.

FIG. 2A illustrates an example usage of the system 200 to provide an immersive environment for a user. The system 200 includes an augmented reality (AR) system 202, a historical experience profile 204 and a user preference profile 206. In the illustrated example, the user is hiking on a desert trail near a canyon with little green foliage but with a substantial drop-off to the user's right as shown in a desert drop-off scene 208. The user may have an inherent fear of heights, for example, that may triggered by or be exacerbated by exposure to the steep drop-off. As the user hikes in the scene, the user employs immersive technology such as AR smart glasses or headset to manage what the user sees and experiences. The AR headset is in communication with the AR system 202, which may be remotely located but accessible over one or more communications networks including a wireless communication network.

In this example, the AR system 202 identifies the location of the user, using, for example, a satellite-based navigation system such as the Global Positioning System (GPS) or using one or more sensors such as a camera, radar, Lidar and others. The AR system 202 retrieves information about the user from the historical experience profile 204. The AR system 202 further retrieves information about the user's preferences from the user preference profile 206. The AR system 202 may thus determine that the user has a fear of heights that may be triggered by the steep drop-off at the particular location where the user is currently hiking. Based on information retrieved from the user preference profile 206, the AR system 202 may determine that the user would prefer a view of a forest with trees and other forest wildlife. The AR system 202, in conjunction with the AR smart glasses or other immersive technology employed by the user, to substitute in the user's field of view a forested scene as shown in image 210 in place of the desert drop-off scene 208. The user may be reassured by the view of the forested scene. Further, by eliminating or substituting for the view of the desert drop-off, the user's fear of heights may be overcome or become manageable. Substitution of a more appealing scene in this manner may be part of training to accommodate and overcome the user's fear of heights. Over time, the substitution may be reduced or modified so that the user gradually comes to see the actual scenery nearby, including the steep drop-off. Because of the behavioral conditioning afforded by the system 200, the user becomes conditioned to the experience of heights, without the attendant fear.

FIG. 2A thus illustrates one use case for a method and apparatus in accordance with the subject disclosure. In this first use case, immersive technology may be used in a system and method to assist with fear and anxiety abatement. For example, such a method may include detection of an item in a scene or in a simulation that triggers anxiety. Detection of anxiety may be by any suitable means, such as by reference to stored data such as the historical experience profile as in FIG. 2A, or by information from wearable devices of the user. For example, if the user wears a smart watch or other device, the device may detect biological information such as the user's heart rate, breathing rate, blood pressure, etc. The AR system 202 correlates the detected anxiety with an item or factor in the current scene. In the illustrated example, the detected anxiety may be provoked by the exposure to a high, unprotected site. In another example, in a VR simulation, the user might be exposed to an object such as a handgun or a poisonous snake that provokes anxiety. The AR system 202 may create test and training situations in simulation or in response to current conditions of the user.

The method for assisting with fear and anxiety abatement may further include steps of lexically or semantically mapping the detected item to a similar item to thereby accommodate or relieve the user's anxiety or to train the user to manage anxiety over the object or situation. For example, in the example of FIG. 2A, the AR system 202 draws a virtual forest scene in the image seen by the user to calm the user with the user-preferred imagery. The virtual forest scene replaces the physical canyon scenery in the immersive experience provided by the AR system 202. In another example, to accommodate the user's fear of heights, the AR system 200 may draw in a virtual guard rail along the unprotected physical edge of the physical path to thereby give the user a sense of reassurance and safety that is absent where the user walks in the desert drop-off scene 208. In another example, if the user has anxiety over poisonous snakes, the AR system 202 may remove the appearance of the snake that is actually present to allay the user's anxiety. In yet another example, to guide the user on a preferred safe path, the AR system 202 may use the AR headset worn by the user to create an immersive view of a virtual green grass path where the user should walk and similarly create a view of virtual hot burning coals where the user should not walk to thereby enhance the path to be taken, the path to avoid, and a preferred solution. The AR system 202 can be used to train and modify behavior of the user.

In a second use case, a method and apparatus in accordance with the subject disclosure may provide for education and performance improvement by a user. For example, in some embodiments, the AR system 202 may identify a task to be completed by the user, including skills to be learned or enhanced and an existing knowledge base of the user. Further, the AR system 202 may identify aspects of the environment that are in effect distractions from the task to be completed, and using AR, block or blur or otherwise negate those distractors. For example, if the user is required to complete a task on electronic components of a rotating engine, the AR system 202 may identify the task to be completed and the functional portions of the engine requiring interaction by the user, such as an electronics package and wiring harness. Similarly, the AR system 202 may identify potential distractors, such as the rotating flywheel, crankshaft and camshaft. To facilitate the completion of the task, the AR system 202 may blur out or blank out images of those rotating components in the image displayed in an AR headset or smart glasses worn by the user. The pertinent components, including the electronics package and wiring harness, are fully displayed and may be visually enhanced to assist the training and performance improvement of the user. The AR system 202 may suppress non-essential features of the displayed environment in the VR view of the environment. Further, the AR system 202 may reduce distractions, including motion and other visual items, that are not essential to the task to be completed. This may include visual features, audible features, and features affecting other senses of the user as well. The effect is to create a cone of silence around the task to be completed in order focus the attention of the user.

In a third use case, a method and apparatus in accordance with the subject disclosure may provide for behavioral improvement for the user by positive reinforcement. This may be particularly useful where the user is training to improve skills or develop new skills, such as for a sport or driving. The AR system 202 can implement a feedback loop that presents virtual content that alters the user's behavior. The user's response can be monitored and stored. In the future, the AR system 202 can be used to manipulate the user's learning experience. In an example, the AR system 202 monitors user performance of a task. In one example, the AR system 202 may be used in a defensive driving instruction scenario. If the driver has an apprehension about other vehicles being too close, the AR system 202 can modify the appearance of the environment so that vehicles nearby are actually made to appear farther away, giving a soothing appearance of an additional buffer between the driver and other vehicles. When the AR system 202 detects what is considered a positive action, the AR system 202 manipulates the view shown to the user to provide what the user will consider to be a more enjoyable view, or an experience that is better in some meaningful way. In addition or instead, the AR system 202 may trigger one or more external systems to provide positive feedback to the user. Some examples of possible positive feedback to the user include activating a device which provides a back massage to the user, or provides audible cheering of a crowd, or provides a visual image of a crowd cheering. Any positive feedback that may reinforce and motivate the user may be implemented. Potential targets for such positive feedback may include correction of aggressive driving by the user, providing visual and audio feedback for particular conditions such as attention deficit disorder (ADD) and other attention disorders. The AR system 202 takes into account the current environment, the user's historical experience and preferences and predilections, and develops a suitable modification to the XR environment in which the user operates.

These and other use cases thus provide for filtering or modulating an input by the user into something more amenable or appropriate to a given situation.

Figure 2B:
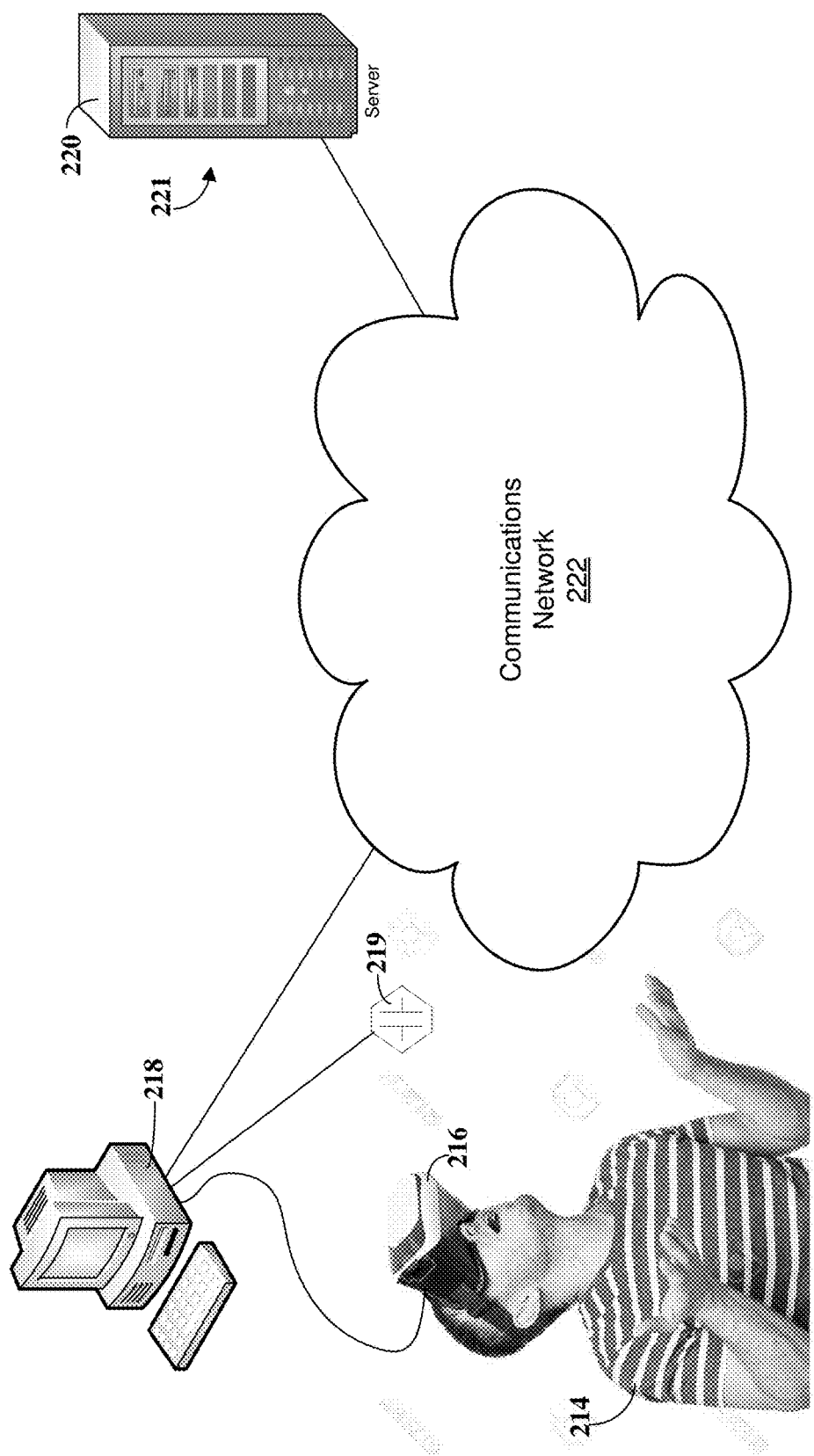
FIG. 2B is a block diagram illustrating an example, non-limiting embodiment of a system functioning within the communication network of FIG. 1 in accordance with various aspects described herein.

FIG. 2B is a block diagram illustrating an example, non-limiting embodiment of a system 212 functioning, for example, within the communication network 100 of FIG. 1 in accordance with various aspects described herein. The system 212 in this embodiment enables a user 214 to interact with an extended reality (XR) environment. The system 212 in this embodiment includes a virtual reality (VR) headset 216 wearable by the user 214, one or more sensors 219, a user computer 218, and an AR server 220 accessible over a communications network 222.

The VR headset 216 enables the user 214 to experience, generally, an XR environment, where XR is a general term intended to encompass XR, VR and augmented reality (AR) systems, equipment and environments. The VR headset 216 generally includes a data processing system including one or more processors, a memory for storing data and instructions, and a communication interface. The VR headset 216 provides visual display to the user 214 and may include one or more display screens within the VR headset 216 to control the view seen by the user 214 and the environment experienced by the user. Further, the VR headset 216 may include a camera for capturing images of the environment of the user. The VR headset 216 may include speakers to provide sound information to the user 214 and the VR headset 216 may include one or more microphones to collect sound information about the environment of the user 214. In other embodiments, the VR headset 216 may be embodied as AR glasses or other wearable devices, or may be operated in conjunction with a fixed display system such as a computer monitor, television or series of display screens in the physical environment with the user 214.

The sensors 219 may include any sort of condition sensing and data collection apparatus suitable for the embodiment of the system. The sensors may include one or more cameras that collect images of the physical environment near the user 214. The cameras may collect visual images, infra-red images and others. The sensors 219 may include environmental sensors that collect information such as temperature, wind speed, orientation or acceleration, or other physical factors of the environment where the user 214 is located. If the user 214 is operating a vehicle, the sensors 219 may detect vehicle speed and steering, acceleration and braking inputs by the user 214. If the vehicle is a driver assisted vehicle, the sensors 219 may collect all information available to the driver assistance system such as images from cameras, navigation and location data, data from Lidar sensors, and others. The sensors 219 may further gather information about the user 214. Such information may include biometric information, such as pulse rate or respiratory rate, skin conductivity, pupil dilation, haptic information about one or more touches of the user 214, and so forth. Thus, the sensors may include or be part of a wearable device such as a watch, belt or harness. Further, such user data may include information about the position, posture and movement of the user. Any sort of data that may be useful by the system 212 for monitoring the user 214 and controlling the XR environment may be sensed by the sensors 219. In some embodiments, the sensors 219 merely sense a condition and report information. In other embodiments, one or more of the sensors 219 may be controllable, such as by the user computer 218.

The user computer 218 is in data communication with the VR headset 216 and the sensors 219. In the illustrated embodiment, the user computer 218 has wireline connections to the VR headset 216 and the sensors 219. In other embodiments, the wireline connections may be supplemented or replaced with one or more wireless connections, such as a WiFi connection according to the IEEE 802.11 family of standards or a Bluetooth connection according to the Bluetooth standard.

The user computer 218 cooperates with the VR headset 216 to provide the XR environment for the user 214. The user computer 218 communicates with the VR headset 216 to provide video information, audio information and other control information to the VR headset 216. The user computer 218 communicates with the sensors 219 to collect information about the physical environment and the user 214. The user computer 218 communicates with the AR server 220 to provide video and other information from the VR headset 216 to the AR server 220 and to provide information and data from the sensors 219 to the AR server 220. The video and data may be sent in any suitable format, including encoding to reduce the amount of data transmitted or encrypted to maintain security of the data. The user computer 218 communicates to the VR headset 216 virtual reality information to the VR headset 216. In some embodiments, the functionality provided by the user computer 218 may be combined with the VR headset 216. In the embodiment of FIG. 2B, the user computer 218 is shown as a desktop computer. However, any suitable processing system, including one or more processors, memory and communications interface, may implement the functions of the user computer 218.

The AR server 220 controls provision of the XR environment to the VR headset 216 for the user 214. The AR server 220 generally includes a processing system including one or more processors, a memory for storing data and instructions and a communications interface. The AR server 220 may be implemented as a single server computer, as multiple server computers at one or multiple locations or in any suitable manner. In the system 212, the AR server 220 implements an augmented reality (AR) engine 221.

The AR server 220 receives over the communications network 222 information about the environment of the user 214, including location information, information about objects in the environment and events occurring in the environment. The AR server 220 in some embodiments may further receive information about the user 214, including biometric information and information about the performance of the user 214. The information may come from the sensors 219, the VR headset 216, or any other source. Under control of the AR engine 221, the AR server 220 provides control information over the communications network 222 including video information, sound information, haptic information and any other information, including instructions and data, to the other components of the system 212 including the user computer 218 and the VR headset 216.

The AR engine 221 develops the XR environment as a combination of the actual environment in which the user 214 is located and a simulated or virtual environment, to achieve ends such as training, education, performance improvement, and behavioral improvement for the user 214. For example, if the user 214 is being trained to operate an apparatus, the AR engine 221 may receive input information describing the user's control inputs for operating the apparatus, for example from the sensors 219. The AR server 220 may react to this input information, to measure the performance or behavior of the user 214. In response, the AR server 220 may modify the XR environment of the user 214. The AR engine 221 creates the XR environment, receives from the user 214 and the XR environment information about the performance of the user 214 in the environment as feedback, and in turn, modifies the XR environment to accomplish the desired end, such as training or behavioral modification for the user 214.

The system 212 may be supplemented with other equipment as desired or required for a particular purpose. For example, the system 212 may include one or more remote cameras to provide video information about the environment of the user. In one embodiment, where the system 212 is enabling education and training of the user on a particular device, one or more cameras may capture images of the device and its location in the environment. The images may be combined with images captured by other cameras, including a camera of the VR headset 216, and with virtual images produced by the AR server 220. Further, the system 212 may be supplemented with other wearable devices to provide additional feedback, such as haptic feedback to the user 214, or further sensors to collect information about the user 214 such as the heart rate and blood pressure of the user 214.

The communications network 222 may include any combination of wireline and wireless communication networks, including but not limited to broadband access network 110, wireless access network 120, voice access network 130 and media access network 140 (FIG. 1). The communications network 222 may include the internet and may provide access to other devices and services as well.

The system 212 thus creates or modifies visual information in an XR experience that correlates to observable behavioral changes in the user 214. Using cameras, microphones and other sensors, the system 212 detects objects in the scene viewed by the user 214 through the VR headset 216. Further, in some embodiments, the system 212 detects user biometric information to determine a status of the user 214, such as user anxiety and experience. The system 212 may draw on learned information available to the system 212, such a machine learning solutions, to understand the status of the user 214 as well as to understand the environment of the user 214 and objects in the environment. The system 212, by cooperation between the AR server 220 and the VR headset 216, may control the visual, audible and otherwise sensible environment of the user 214. For example, in the visual realm, the system 212 can substitute or erase non-essential objects for a task to be performed by the user. Further, the system 212 can provide immersive reinforcement for behavior of the user 214. This can be done for a wide variety of reasons, including to train the user 214 to new behaviors or to modify the user 214 to avoid past bad behaviors or to improve future behaviors for the user 214.

Figure 2C:
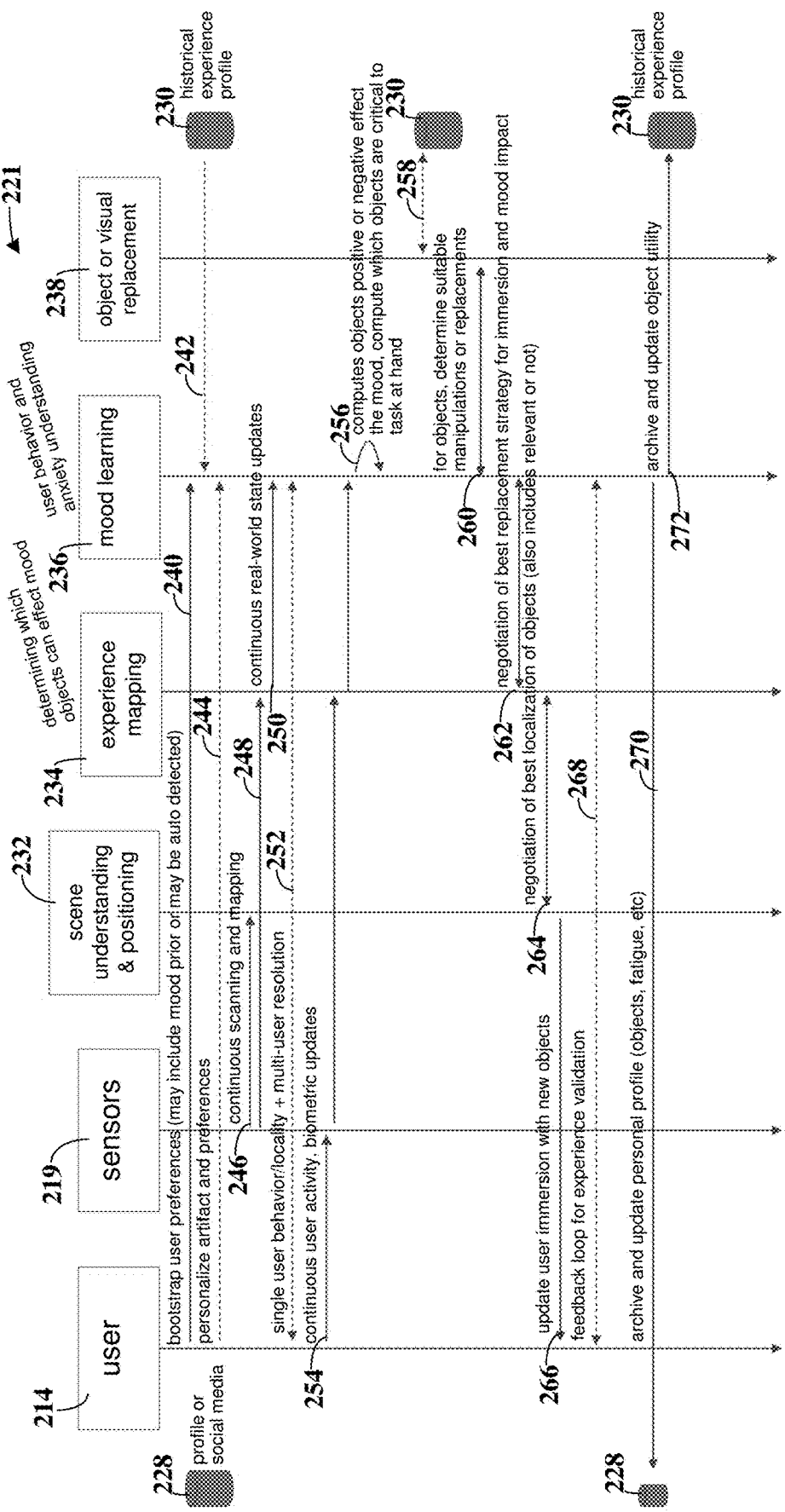
FIG. 2C depicts an illustrative embodiment of a method in accordance with various aspects described herein.

FIG. 2C depicts an illustrative embodiment of a method 224 in accordance with various aspects described herein. The method 224 in general creates and controls an extended reality (XR) environment or immersive experience for the user 214. The user 214 experiences an immersive scene which includes some portions of the physical environment where the user 214 is located, along with some virtual objects or elements that are created, selected, modified and controlled by the AR engine 221 operating on the server 220.

The method 224 may be implemented by any suitable combination of components. In one embodiment, the method 224 may be implemented by components of system 212 in FIG. 2B, including sensors 219 in the environment of user 214 and AR server 220. Further, the exemplary embodiment of FIG. 2C includes a profile or social media database 228 and a historical experience profile database 230. The AR server 220 responds to data and instructions and implements an AR engine 221 including a number of functional stages or modules. These include in the embodiment of FIG. 2C a scene understanding and positioning module 232, an experience mapping module 234, a mood learning module 236 and an object or visual replacement module 238. The modules implemented by AR server 220 in the AR engine 221 are exemplary only and may be substituted or replaced by any suitable modules or combination of functional elements necessary to perform the required operations.

Initially, the system 212 must obtain or develop an understanding of the environment surrounding the user, including information about where the user is, what else is in the environment and what is going on in the environment. This includes, for example, an understanding of objects and how they are moving. Such information may also include information about a task the user is to accomplish or is engaged in and information about user preferences. This may further include historical information and social media profiles, for example. Such surrounding information may be collected by or provided to the AR server 220.

In the embodiment of FIG. 2C, the method begins at step 240. Information about user preferences is communicated from the user 214 to the mood learning module 236 of the AR server 220 in order to bootstrap the learning of user preferences. The mood learning module 236 operates to understand the behavior of the user and to understand anxiety and mental state of the user 214, which collectively may be termed the mood of the user 214. The mood learning module 236 further operates to understand changes to the user mood over time, as well as to understand reasons for the changes to user mood. The user preference information may be provided directly by the user 214. The user preferences may include any information about the user that may be pertinent to the task or training or situation. The information may be communicated from a device of the user 214, such as a cellular phone or other mobile device. The information may be communicated from the user, collected and stored.

In some embodiments, the information may be retrieved from a source such as the profile or social media database 228. The profile and social media database 228 may store information collected from social media accounts maintained by the user 214 or by people or institutions, such as an employer, associated with the user 214. The profile and social media database 228 may obtain information by, for example, crawling the internet or by accessing stored information about the user in other network locations. The profile and social media database 228 may store information unique to users including user 214 that may be used during a training or behavioral modification session by the AR server 220. For example, if the user 214 is moving to a new location and is anxious about the move, the AR server 220 may provide images of children of the user 214 to serve as a reassuring image in the XR environment related to the move. In other examples, the AR server 220 may decide what to show to the user 214 or what to mask from view by the user 214 in the XR environment based on information contained in the profile and social media database 228.

In some embodiments, the AR server 220 retrieves information about the mood of the user 214 during a previous time. For example, if the user 214 is undergoing behavioral conditioning in multiple XR sessions, the AR server 220 may have stored information from a previous session and may retrieve the stored information. Such information may serve, for example, as a baseline for the current mood or mental state of the user 214.

In some embodiments, the process of bootstrapping user preferences may be done by accessing information about individuals who are demographically similar to the user 214. Individuals of the same age and economic status and geographic location, and so on, may have preferences matching those of the user. The collected information of such similar individuals may be useful for bootstrapping operation of the AR server 220. Optionally, the engagement and interactions of multiple users could be pooled with others or aggregated to define behavioral preferences.

Further, at step 242, the mood learning module 236 of the AR server 220 obtains historical information about the user, the task or training or other situation. The historical information may be any information useful to understanding the current situation. In the embodiment of FIG. 2C, the historical information is obtained from historical experience profile database 230. The historical experience profile database 230 in some embodiments contains information about how the user 214 responded to certain augmented environments in the past. Also in some embodiments, the historical experience profile database 230 may store information about learning tasks involving multiple users or aggregated information about how multiple users reacted to the training data. However, the historical information may be obtained from any suitable source in addition to the historical experience profile database 230.

At step 244, the user 214 may optionally personalize the preference information provided to the mood learning module 236. This may permit the user to better control information provided to the AR server 220 and to tailor the information about the user 214 that is used by the mood learning module.

At step 246, the AR server 220 begins a process of continuously scanning and mapping the environment of the user 214. The scene understanding and positioning module 232 operates initially to understand the scene where the user 214 is located and functioning, including the physical environment. This may be done, for example, using information available from cameras and sensors 219 in the environment. The scene understanding and positioning module 232 receives information including sensor information from the sensors 219 and identifies the location of the environment, the items in the environment, and activity in the environment. Further, the scene understanding and positioning module 232 determines information about surfaces, rough objects and placement of objects in the physical environment. In some examples, this may be done initially in generic or abstract terms, until more information becomes available. In general, the scene understanding and positioning module 232 operates to map the XR environment or scene where the user 214 is located. In some embodiments, and in some applications, this process may continue throughout operation of the method 224 as objects change or move or as the mood of the user 214 changes. The scene understanding and positioning module 232 may establish and maintain a map of the physical environment and the virtual environment that together form the XR environment, and update the map during progress of the method 224.

At step 248, some or all of the scanning and mapping information provided to the scene understanding and positioning module 232 is similarly provided to the experience mapping module 234 of the AR server 220. The experience mapping module 234 operates to determine which objects in the XR environment can affect the mood of the user 214 and how virtual content in the XR environment can affect the mood of the user 214.

At step 250, the experience mapping module 234 provides continuous, real-world updates to the mood learning module 236. The updating process is based on additional information received by the experience mapping module 234, such as updates about the activities of the user 214, updates about objects in the environment of the user 214 and the user's interaction with such objects, and so forth. Such information may be reflective of the mood of the user 214 or may be useful to the mood learning module 236 for discerning the mood or changes in the mood of the user 214.

At step 252, an optional single user locality and multi-user resolution operation are implemented between the user 214 and the mood learning module 236. In some applications, more than a single user may be the subject of training or behavior modification.

At step 254, the AR server 220 receives continuous updates of information about activity of the user 214. These may include biometric updates such as information about the heartrate, blood pressure or pupil dilation of the user 214, or information about the position or posture or activities of the user 214. The information may come from any suitable source such as the user 214, sensors 219, cameras viewing the user 214 and the environment or scene. The user activity information may be provided to the experience mapping module 234 and the mood learning module 236. This continues as the AR engine 221 modifies the XR environment by changing visual, audible and other aspects of the XR environment.

For example, if the user is being conditioned to overcome a fear of a particular object, such as a spider, the AR server 220 may progressively expose the user 214 to images and experiences of spiders in the XR environment experienced by the user 214. The attitude or fear level or comfort level (generally, the mood) of the user 214 may vary as the experience of the user 214 with the object is varied by the AR engine 221. The mood of the user will be reflected in the user activity information and the biometric updates. For example, the user may cringe in anxiety and this change in facial expression will be reported at step 254. Or, the heartrate of the user 214 may decrease because the user is becoming more comfortable with spiders, and this biometric change may be reported and noted. In another example, the user may put his arms up in fear, and this gesture may be detected. For example, a camera observing the user may provide images of the user, including the fear gesture, to the AR engine 221. The mood learning module 236 may discern from the gesture, including the change in the gesture of the user 214, that the user 214 is experiencing fear.

In some embodiments, the mood learning module 236 may include one or more machine learning models to process, interpret and understand the mood of the user 214. Inputs to the machine learning model, and to the mood learning module 236 more generally, include information such as biometric information of the user and actions of the user 214, such as a grasp by the user 214 to reach something or a facial expression or eye movements of the user 214.

At step 256, the mood learning module 236 determines an effect on the mood of the user 214 based on the reported biometric updates and user activity updates from step 254. The mood learning module 236 determines if an object in the XR environment produces a negative effect or positive effect on the mood of the user. For example, a positive effect may be an effect which modifies the behavior of the user 214 in the manner desired. A negative effect on the user 214 may be an effect which modifies the mood of the user 214 in a manner other than what was intended. A neutral effect may be considered either a positive effect or a negative effect. Step 256 and related steps may form a probabilistic mapping of new objects that may be included in the XR environment.

In some embodiments, the AR server 220 operates to insert virtual objects into the XR environment of the user 214 and determines how the inserted objects modify the behavior or mood of the user 214. Objects that may be inserted may include the scenic background or, in an educational context, by highlighting an object or hiding an object, or depicting an object that the user is familiar with. One goal of the operation of the method might be to put the user 214 into a better frame of mind regarding a task or situation. The inserted objects do not necessarily need to be used in the experience or the environment, but the inserted objects may be used to improve the mental state of the user 214 or the amenability of the user 214 to the task at hand.

At step 258, the historical experience profile database 230 may optionally be accessed to retrieve a contextual history for the user 214 and interactions of the user 214 to predict when a next XR immersion experience object is realized. At step 260, the mood learning module 236 and the object or visual replacement module 238 cooperate to determine suitable manipulations or replacement of objects in the XR environment. For example, based on information about the mood of the user 214, the mood learning module 236 and the object or visual replacement module 238 may determine to place an object in the XR environment with the user 214. The user's activity and the nature of the task (such as running or engagement), affect the importance of the objects in the scene and their location. The mood learning module 236 and the object or visual replacement module 238 will weigh the complexity of the artificially generated object.

In some examples, user profile media, such as photos, video files or audio files, can be retrieved to contribute to the context of the scene and objects. For example, if the user is running toward an object in the scene, the scene understanding and positioning module 232 may place an image of an object of desire to the user, such as a picture of a family member, in the rendered environment. The goal or purpose is to create in the user a particular mood or sentiment or response, such as happiness or willingness or determination. The mood or sentiment or response is responsive to the object of desire. In some examples, the user profile media may be retrieved, for example, from the profile or social media database 228.

Based on the determined effect on the user 214, the mood learning module 236 and the object or visual replacement module 238 may determine to move or reposition the object in the XR environment. For example, the modules may determine if putting a particular object into the immersive environment makes the situation more enjoyable or less enjoyable for the user, or if too many objects have been added to the scene. Similarly, at step 262, the mood learning module 236 and the experience mapping module 234 cooperate to determine a best placement strategy for placing objects in the XR environment to effect the mood of the user 214. Still further, at step 264, the experience mapping module 234 and the scene understanding and positioning module 232 may cooperate to determine a best localization of objects in the XR environment.

The steps of the method 224 permit a reweighing of the probabilities of possibly generated objects with an understanding of user behavior and anxiety. Step 254 provides continuous updates of information about use activity and biometric values. This permits the mood learning module 236 to determine the effect of objects in the immersive environment on the mood of the user 214. The mood reflects in part user anxiety and the estimation by the mood learning module 236 of the mood of the user 214 permits the mood learning module 236 to cooperate with the experience mapping module 234 to determine the best object placement strategy, including the probable outcomes from placement of particular objects in the scene.

For example, the mood learning module 236 and the experience mapping module 234, or other features of the AR server 220, may cooperate to plan objects and their utility to the user, including placement of additional objects, replacement of existing objects or visual manipulation of the immersive experience. In another example, based on user cognition and history, the mood learning module 236 and the experience mapping module 234 may consider reuse of certain objects in the XR experience. This avoids the need to regenerate such objects, thereby reducing repeated computer processor cycles and reducing memory storage requirements. However, the mood learning module 236 and the experience mapping module 234 may focus on avoiding too much repeated exposure by the user to particular objects.

In some embodiments, the AR server 220 may include features to emphasize real-world aspects of the immersive experience. For example, as the XR environment is assembled by the mood learning module 236 and the experience mapping module 234, the objects in the XR environment may follow real-world physics. That is, if a virtual object is falling without support, it will fall according to actual gravity. If two objects collide, they will deform and bounce apart in a manner that appears real according to conventional real-world physics.

In some embodiments, the mood learning module 236 and the experience mapping module 234 may use pre-existing virtual models of real-world objects. This may improve scene simulation for the user 214, causing the scene to appear more realistic. Moreover, the AR engine 221 may retrieve from a database or other storage data defining a virtual model of an object in order to reduce the data processing time and memory required for generating the XR environment or modifying the XR environment and communicating data representing the XR environment to the user 214. For example, in some embodiments, the AR engine 221 may retrieve from a database data defining a wireframe outline of an object such as a ball or automobile, and retrieve additional data representing texture or color or other visual aspects of the object. The data for the wireframe outline may be rapidly and efficiently combined with the data for the visual aspects, reducing the amount of time required to generate the scene. This can be an important technical advantage in an XR environment where the user 214 is engaging in real-world activities such as in FIG. 2A where the user is hiking in a potentially dangerous environment and the AR server 220 must provide real-time updates to the VR headset or other equipment of the user 214. Reducing the amount of data to be processed by retrieving and modifying pre-existing virtual components and combining the processed virtual components with physical or real-world elements of the XR environment may assist the AR engine 221 in responding to real-world, physical changes.

In another example, the AR engine 221 may retrieve from storage pre-existing data for contextual objects to enable better scene simulation. In one example, where the XR scene to be simulated is a locker room, the AR engine 221 may retrieve from a database pre-existing data defining all objects for the locker room to thereby convert an empty room in which the user 214 is located to an XR locker room. In this manner, by retrieving all or substantially all objects as pre-existing data for the scene, the AR engine 221 may more rapidly and efficiently instantiate the XR environment. The response time is improved and the reality of the simulation is enhanced. Moreover, the amount of data that must be retrieved is reduced, along with the amount of data that must be communicated by the AR server 220 over the communications network 222 to the VR headset 216 or the user computer 218.

In other examples, the AR engine 221 may employ one or more visual effects to adjust or adapt the appearance of objects in the XR environment. For example, foveated rendering includes rendering an image with different resolutions. For example, the AR engine 221 may render at a first resolution or higher resolution or sharpen the resolution of portions of the image on which the vision of the user 214 is focused and reduce the resolution, or render at a second, lower resolution, other parts of the image. In this manner, the portions of the image at the first, higher resolution will stand out in the image and catch the attention of the user 214. The portions of the image at the second, lower resolution will, in effect, fade into the background. In other examples, the AR engine 221 may blur some or all of the image presented to the user 214. This may be done, for example if the user is in an active state or to avoid exposure fatigue for the user 214. Also, foveation or blurring may be used to focus the view and the attention of the user 214, and may provide a technical advantage by reducing the amount of data that must be processed and communicated from the AR server 220 to the user 214. For example, defining in high definition an image of just a small part of the space around the user requires much less data and processing power and memory storage than does a high definition of a fully surrounding view of the user.

At step 266, information is communicated to the user 214 to update the user immersion with new or changed objects. The updated information is based on the negotiation between the experience mapping module 234 and the scene understanding and positioning module 232. For example, if the negotiation concludes to add a new object to the XR environment, data to convey that change is communicated to the equipment providing the XR immersion. In the exemplary system of FIG. 2B, the information is communicated from the AR server 220 to the user computer 218 and the VR headset 216 worn by the user 214 over the communication network 222.

As indicated at step 268, the set of steps including step 254, step 256, step 258, step 260, step 262, step 264 and step 266 may form a feedback loop for validating the experience of the user 214. The feedback loop may include continuously receiving information about the condition of the user 214, including image information from cameras and biometric information from sensors 219, computing positive or negative effects on the user 214 of objects in the immersive experience and determining which objects are critical to the task at hand and which are less significant. The feedback loop may further include determining suitable manipulations or replacements of the objects and a best replacement strategy to affect the mood of the user 214. The feedback loop further include determining a best localization and providing an update to the user with new or changed objects for the immersive experience. In this manner, the method 224 may include a trial and error process of inserting objects into the immersive environment, detecting based on the reported user activity and biometric information an effect of the inserted object and interpreting the reported activity and biometric information as feedback to the inserted object.

At step 270, the mood learning module 236 may archive data about the user, for example, in the profile or social media database 228. The archived data may include information learned about the user, such as the effect on the user of objects inserted in the immersive experience, where the effect is determined from information from the sensors 219, cameras viewing the physical environment of the user and biometric sensors. Similarly, at step 272, the mood learning module 236 will archive data about the user and the immersive experience, for example, in the historical experience profile database 230.

The systems 200, 212 and method 224 illustrated and described herein provide a number of useful benefits. In one example, the systems and method allow expression of anxiety and experience attributes both from manual user input as well as learned attributes from user behavior across different immersion experiences. The system and method may use one or more machine learning models to learn about the user from user behavior and other information collected from the user. In other examples, better performance by the user may be realized with assistive objects artificially created by the system and method. Examples include hiding from the user those things or objects that may be distracting or have a negative impact on the user during the task at hand.

Other benefits obtained by the systems and methods include providing objects that can enhance the user's mood during an immersive experience. For example, objects identified and provided virtually in the XR environment can have the effect of making a frightening object not seem as intimidating to the user. This can operate to modify the user's behavior or response to an object or a situation.

Another benefit provided by the systems and method include creating a more personable and realistic XR environment through mood matching. For example, the AR server 220 can determine the user's current mood and modify the environment to match that mood. In one example, the system can add happy characters to a joyful task to be performed by the user. In another example, the system can add dark and morose objects in a suspenseful experience.

Another benefit provided by the systems and method include, though complementary objects for a task, providing gradual "operant conditioning" to modify a mood and object satisfaction. More specifically, for therapy and behavioral adjustment, such as in one example, quitting smoking, certain objects can be added or modified to accelerate the behavior modification.

While for purposes of simplicity of explanation, the respective processes are shown and described as a series of blocks in FIG. 2C, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Referring now to FIG. 3, a block diagram is shown illustrating an example, non-limiting embodiment of a virtualized communication network 300 in accordance with various aspects described herein. In particular a virtualized communication network is presented that can be used to implement some or all of the subsystems and functions of system 100, the subsystems and functions of system 200 and system 212 and method 224 presented in FIGS. 1, 2A, 2B, 2C, and 3. For example, virtualized communication network 300 can facilitate in whole or in part providing an immersive environment for a user that includes at least some virtual objects in the immersive environment. The mood of the user may be monitored and objects may be modified to adjust the mood of the user. This can be done, for example, the train the user or modify the user's behavior in certain situations.

In particular, a cloud networking architecture is shown that leverages cloud technologies and supports rapid innovation and scalability via a transport layer 350, a virtualized network function cloud 325 and/or one or more cloud computing environments 375. In various embodiments, this cloud networking architecture is an open architecture that leverages application programming interfaces (APIs); reduces complexity from services and operations; supports more nimble business models; and rapidly and seamlessly scales to meet evolving customer requirements including traffic growth, diversity of traffic types, and diversity of performance and reliability expectations.

In contrast to traditional network elements—which are typically integrated to perform a single function, the virtualized communication network employs virtual network elements (VNEs) 330, 332, 334, etc. that perform some or all of the functions of network elements 150, 152, 154, 156, etc. For example, the network architecture can provide a substrate of networking capability, often called Network Function Virtualization Infrastructure (NFVI) or simply infrastructure that is capable of being directed with software and Software Defined Networking (SDN) protocols to perform a broad variety of network functions and services. This infrastructure can include several types of substrates. The most typical type of substrate being servers that support Network Function Virtualization (NFV), followed by packet forwarding capabilities based on generic computing resources, with specialized network technologies brought to bear when general purpose processors or general purpose integrated circuit devices offered by merchants (referred to herein as merchant silicon) are not appropriate. In this case, communication services can be implemented as cloud-centric workloads.

As an example, a traditional network element 150 (shown in FIG. 1), such as an edge router can be implemented via a VNE 330 composed of NFV software modules, merchant silicon, and associated controllers. The software can be written so that increasing workload consumes incremental resources from a common resource pool, and moreover so that it's elastic: so the resources are only consumed when needed. In a similar fashion, other network elements such as other routers, switches, edge caches, and middle-boxes are instantiated from the common resource pool. Such sharing of infrastructure across a broad set of uses makes planning and growing infrastructure easier to manage.

In an embodiment, the transport layer 350 includes fiber, cable, wired and/or wireless transport elements, network elements and interfaces to provide broadband access 110, wireless access 120, voice access 130, media access 140 and/or access to content sources 175 for distribution of content to any or all of the access technologies. In particular, in some cases a network element needs to be positioned at a specific place, and this allows for less sharing of common infrastructure. Other times, the network elements have specific physical layer adapters that cannot be abstracted or virtualized, and might require special DSP code and analog front-ends (AFEs) that do not lend themselves to implementation as VNEs 330, 332 or 334. These network elements can be included in transport layer 350.

The virtualized network function cloud 325 interfaces with the transport layer 350 to provide the VNEs 330, 332, 334, etc. to provide specific NFVs. In particular, the virtualized network function cloud 325 leverages cloud operations, applications, and architectures to support networking workloads. The virtualized network elements 330, 332 and 334 can employ network function software that provides either a one-for-one mapping of traditional network element function or alternately some combination of network functions designed for cloud computing. For example, VNEs 330, 332 and 334 can include route reflectors, domain name system (DNS) servers, and dynamic host configuration protocol (DHCP) servers, system architecture evolution (SAE) and/or mobility management entity (MME) gateways, broadband network gateways, IP edge routers for IP-VPN, Ethernet and other services, load balancers, distributers and other network elements. Because these elements don't typically need to forward large amounts of traffic, their workload can be distributed across a number of servers—each of which adds a portion of the capability, and overall which creates an elastic function with higher availability than its former monolithic version. These virtual network elements 330, 332, 334, etc. can be instantiated and managed using an orchestration approach similar to those used in cloud compute services.

The cloud computing environments 375 can interface with the virtualized network function cloud 325 via APIs that expose functional capabilities of the VNEs 330, 332, 334, etc. to provide the flexible and expanded capabilities to the virtualized network function cloud 325. In particular, network workloads may have applications distributed across the virtualized network function cloud 325 and cloud computing environment 375 and in the commercial cloud, or might simply orchestrate workloads supported entirely in NFV infrastructure from these third party locations.

Figure 4:
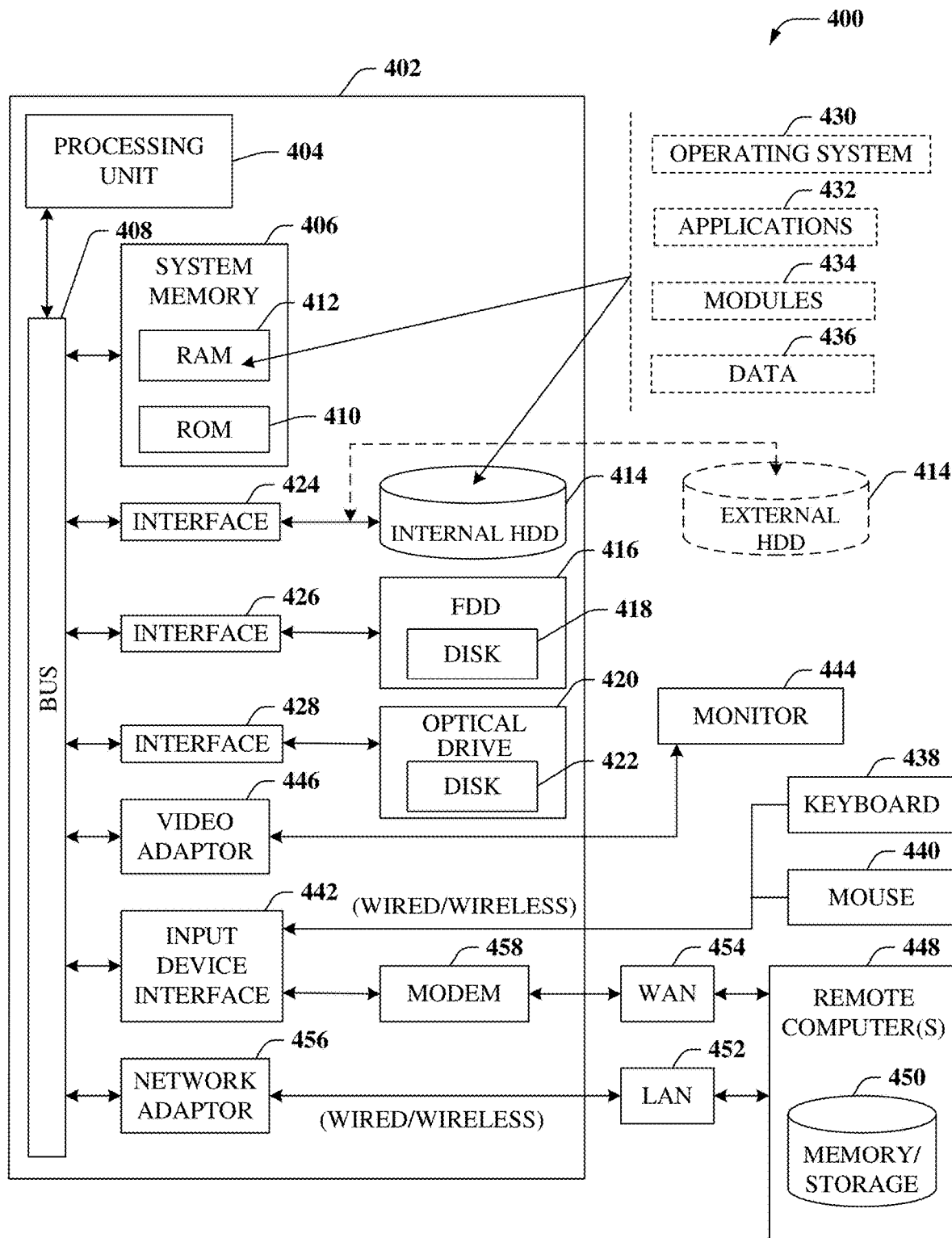
FIG. 4 is a block diagram of an example, non-limiting embodiment of a computing environment in accordance with various aspects described herein.

Turning now to FIG. 4, there is illustrated a block diagram of a computing environment in accordance with various aspects described herein. In order to provide additional context for various embodiments of the embodiments described herein, FIG. 4 and the following discussion are intended to provide a brief, general description of a suitable computing environment 400 in which the various embodiments of the subject disclosure can be implemented. In particular, computing environment 400 can be used in the implementation of network elements 150, 152, 154, 156, access terminal 112, base station or access point 122, switching device 132, media terminal 142, and/or VNEs 330, 332, 334, etc. Each of these devices can be implemented via computer-executable instructions that can run on one or more computers, and/or in combination with other program modules and/or as a combination of hardware and software. For example, computing environment 400 can facilitate in whole or in part providing an immersive environment for a user that includes at least some virtual objects in the immersive environment. The mood of the user may be monitored and objects may be modified to adjust the mood of the user. This can be done, for example, the train the user or modify the user's behavior in certain situations.

Generally, program modules comprise routines, programs, components, data structures, etc., that perform particular tasks or implement particular abstract data types. Moreover, those skilled in the art will appreciate that the methods can be practiced with other computer system configurations, comprising single-processor or multiprocessor computer systems, minicomputers, mainframe computers, as well as personal computers, hand-held computing devices, microprocessor-based or programmable consumer electronics, and the like, each of which can be operatively coupled to one or more associated devices.

As used herein, a processing circuit includes one or more processors as well as other application specific circuits such as an application specific integrated circuit, digital logic circuit, state machine, programmable gate array or other circuit that processes input signals or data and that produces output signals or data in response thereto. It should be noted that while any functions and features described herein in association with the operation of a processor could likewise be performed by a processing circuit.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically comprise a variety of media, which can comprise computer-readable storage media and/or communications media, which two terms are used herein differently from one another as follows. Computer-readable storage media can be any available storage media that can be accessed by the computer and comprises both volatile and nonvolatile media, removable and non-removable media. By way of example, and not limitation, computer-readable storage media can be implemented in connection with any method or technology for storage of information such as computer-readable instructions, program modules, structured data or unstructured data.

Computer-readable storage media can comprise, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage or other magnetic storage devices or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and comprises any information delivery or transport media. The term "modulated data signal" or signals refers to a signal that has one or more of its characteristics set or changed in such a manner as to encode information in one or more signals. By way of example, and not limitation, communication media comprise wired media, such as a wired network or direct-wired connection, and wireless media such as acoustic, RF, infrared and other wireless media.

With reference again to FIG. 4, the example environment can comprise a computer 402, the computer 402 comprising a processing unit 404, a system memory 406 and a system bus 408. The system bus 408 couples system components including, but not limited to, the system memory 406 to the processing unit 404. The processing unit 404 can be any of various commercially available processors. Dual microprocessors and other multiprocessor architectures can also be employed as the processing unit 404.

The system bus 408 can be any of several types of bus structure that can further interconnect to a memory bus (with or without a memory controller), a peripheral bus, and a local bus using any of a variety of commercially available bus architectures. The system memory 406 comprises ROM 410 and RAM 412. A basic input/output system (BIOS) can be stored in a non-volatile memory such as ROM, erasable programmable read only memory (EPROM), EEPROM, which BIOS contains the basic routines that help to transfer information between elements within the computer 402, such as during startup. The RAM 412 can also comprise a high-speed RAM such as static RAM for caching data.

The computer 402 further comprises an internal hard disk drive (HDD) 414 (e.g., EIDE, SATA), which internal HDD 414 can also be configured for external use in a suitable chassis (not shown), a magnetic floppy disk drive (FDD) 416, (e.g., to read from or write to a removable diskette 418) and an optical disk drive 420, (e.g., reading a CD-ROM disk 422 or, to read from or write to other high capacity optical media such as the DVD). The HDD 414, magnetic FDD 416 and optical disk drive 420 can be connected to the system bus 408 by a hard disk drive interface 424, a magnetic disk drive interface 426 and an optical drive interface 428, respectively. The hard disk drive interface 424 for external drive implementations comprises at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 402, the drives and storage media accommodate the storage of any data in a suitable digital format. Although the description of computer-readable storage media above refers to a hard disk drive (HDD), a removable magnetic diskette, and a removable optical media such as a CD or DVD, it should be appreciated by those skilled in the art that other types of storage media which are readable by a computer, such as zip drives, magnetic cassettes, flash memory cards, cartridges, and the like, can also be used in the example operating environment, and further, that any such storage media can contain computer-executable instructions for performing the methods described herein.

A number of program modules can be stored in the drives and RAM 412, comprising an operating system 430, one or more application programs 432, other program modules 434 and program data 436. All or portions of the operating system, applications, modules, and/or data can also be cached in the RAM 412. The systems and methods described herein can be implemented utilizing various commercially available operating systems or combinations of operating systems.

A user can enter commands and information into the computer 402 through one or more wired/wireless input devices, e.g., a keyboard 438 and a pointing device, such as a mouse 440. Other input devices (not shown) can comprise a microphone, an infrared (IR) remote control, a joystick, a game pad, a stylus pen, touch screen or the like. These and other input devices are often connected to the processing unit 404 through an input device interface 442 that can be coupled to the system bus 408, but can be connected by other interfaces, such as a parallel port, an IEEE 1394 serial port, a game port, a universal serial bus (USB) port, an IR interface, etc.

A monitor 444 or other type of display device can be also connected to the system bus 408 via an interface, such as a video adapter 446. It will also be appreciated that in some embodiments, a monitor 444 can also be any display device (e.g., another computer having a display, a smart phone, a tablet computer, etc.) for receiving display information associated with computer 402 via any communication means, including via the Internet and cloud-based networks. In addition to the monitor 444, a computer typically comprises other peripheral output devices (not shown), such as speakers, printers, etc.

The computer 402 can operate in a networked environment using logical connections via wired and/or wireless communications to one or more remote computers, such as a remote computer(s) 448. The remote computer(s) 448 can be a workstation, a server computer, a router, a personal computer, portable computer, microprocessor-based entertainment appliance, a peer device or other common network node, and typically comprises many or all of the elements described relative to the computer 402, although, for purposes of brevity, only a remote memory/storage device 450 is illustrated. The logical connections depicted comprise wired/wireless connectivity to a local area network (LAN) 452 and/or larger networks, e.g., a wide area network (WAN) 454. Such LAN and WAN networking environments are commonplace in offices and companies, and facilitate enterprise-wide computer networks, such as intranets, all of which can connect to a global communications network, e.g., the Internet.

When used in a LAN networking environment, the computer 402 can be connected to the LAN 452 through a wired and/or wireless communication network interface or adapter 456. The adapter 456 can facilitate wired or wireless communication to the LAN 452, which can also comprise a wireless AP disposed thereon for communicating with the adapter 456.

When used in a WAN networking environment, the computer 402 can comprise a modem 458 or can be connected to a communications server on the WAN 454 or has other means for establishing communications over the WAN 454, such as by way of the Internet. The modem 458, which can be internal or external and a wired or wireless device, can be connected to the system bus 408 via the input device interface 442. In a networked environment, program modules depicted relative to the computer 402 or portions thereof, can be stored in the remote memory/storage device 450. It will be appreciated that the network connections shown are example and other means of establishing a communications link between the computers can be used.

The computer 402 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This can comprise Wireless Fidelity (Wi-Fi) and BLUETOOTH® wireless technologies. Thus, the communication can be a predefined structure as with a conventional network or simply an ad hoc communication between at least two devices.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, n, ac, ag, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands for example or with products that contain both bands (dual band), so the networks can provide real-world performance similar to the basic 10BaseT wired Ethernet networks used in many offices.

Figure 5:
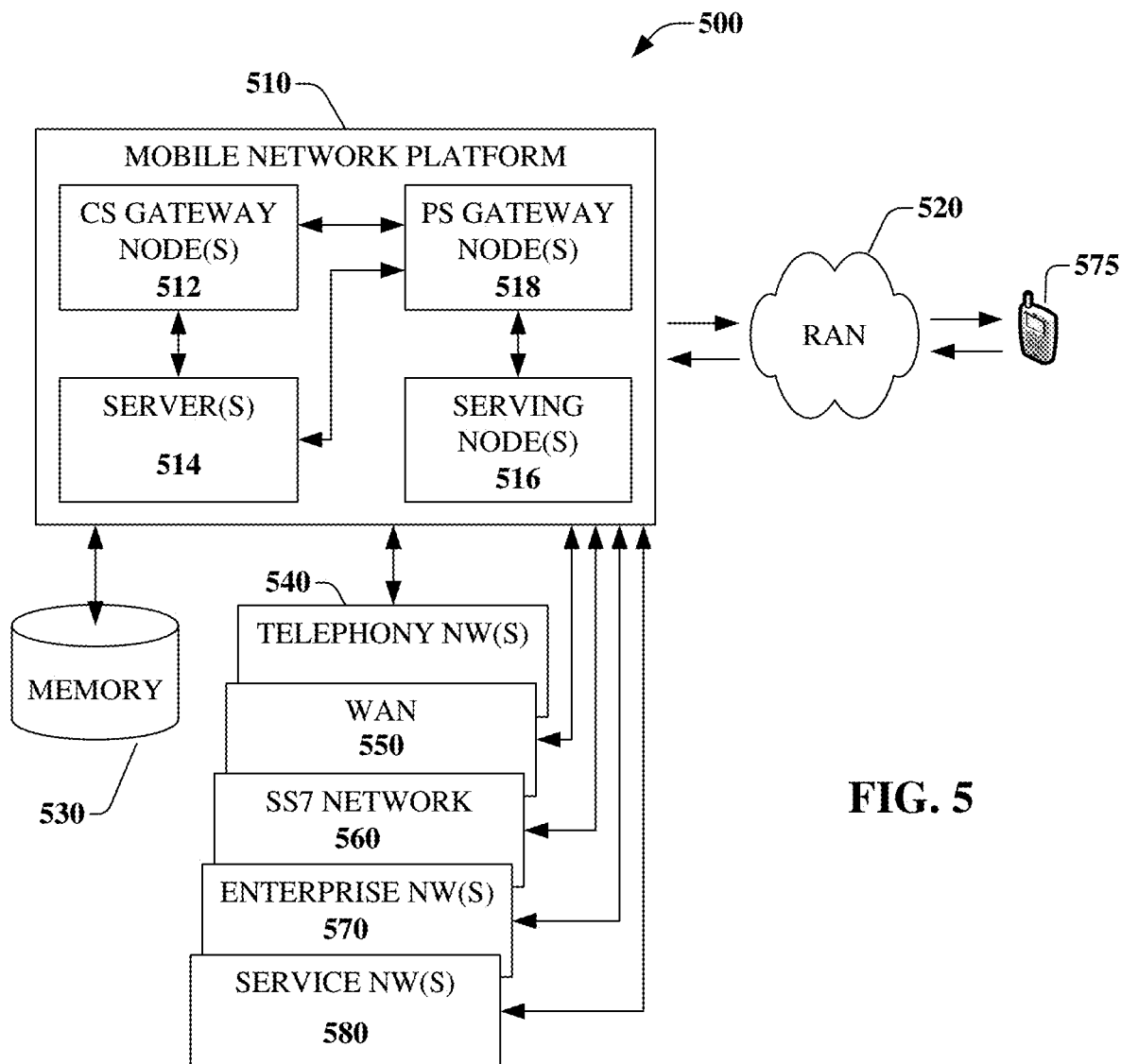
FIG. 5 is a block diagram of an example, non-limiting embodiment of a mobile network platform in accordance with various aspects described herein.

Turning now to FIG. 5, an embodiment 500 of a mobile network platform 510 is shown that is an example of network elements 150, 152, 154, 156, and/or VNEs 330, 332, 334, etc. For example, platform 510 can facilitate in whole or in part providing an immersive environment for a user that includes at least some virtual objects in the virtual environment. The mood of the user may be monitored and objects may be modified to adjust the mood of the user. This can be done, for example, the train the user or modify the user's behavior in certain situations. In one or more embodiments, the mobile network platform 510 can generate and receive signals transmitted and received by base stations or access points such as base station or access point 122. Generally, mobile network platform 510 can comprise components, e.g., nodes, gateways, interfaces, servers, or disparate platforms, that facilitate both packet-switched (PS) (e.g., internet protocol (IP), frame relay, asynchronous transfer mode (ATM)) and circuit-switched (CS) traffic (e.g., voice and data), as well as control generation for networked wireless telecommunication. As a non-limiting example, mobile network platform 510 can be included in telecommunications carrier networks, and can be considered carrier-side components as discussed elsewhere herein. Mobile network platform 510 comprises CS gateway node(s) 512 which can interface CS traffic received from legacy networks like telephony network(s) 540 (e.g., public switched telephone network (PSTN), or public land mobile network (PLMN)) or a signaling system #7 (SS7) network 560. CS gateway node(s) 512 can authorize and authenticate traffic (e.g., voice) arising from such networks. Additionally, CS gateway node(s) 512 can access mobility, or roaming, data generated through SS7 network 560; for instance, mobility data stored in a visited location register (VLR), which can reside in memory 530. Moreover, CS gateway node(s) 512 interfaces CS-based traffic and signaling and PS gateway node(s) 518. As an example, in a 3GPP UMTS network, CS gateway node(s) 512 can be realized at least in part in gateway GPRS support node(s) (GGSN). It should be appreciated that functionality and specific operation of CS gateway node(s) 512, PS gateway node(s) 518, and serving node(s) 516, is provided and dictated by radio technologies utilized by mobile network platform 510 for telecommunication over a radio access network 520 with other devices, such as a radiotelephone 575.

In addition to receiving and processing CS-switched traffic and signaling, PS gateway node(s) 518 can authorize and authenticate PS-based data sessions with served mobile devices. Data sessions can comprise traffic, or content(s), exchanged with networks external to the mobile network platform 510, like wide area network(s) (WANs) 550, enterprise network(s) 570, and service network(s) 580, which can be embodied in local area network(s) (LANs), can also be interfaced with mobile network platform 510 through PS gateway node(s) 518. It is to be noted that WANs 550 and enterprise network(s) 570 can embody, at least in part, a service network(s) like IP multimedia subsystem (IMS). Based on radio technology layer(s) available in technology resource(s) or radio access network 520, PS gateway node(s) 518 can generate packet data protocol contexts when a data session is established; other data structures that facilitate routing of packetized data also can be generated. To that end, in an aspect, PS gateway node(s) 518 can comprise a tunnel interface (e.g., tunnel termination gateway (TTG) in 3GPP UMTS network(s) (not shown)) which can facilitate packetized communication with disparate wireless network(s), such as Wi-Fi networks.

In embodiment 500, mobile network platform 510 also comprises serving node(s) 516 that, based upon available radio technology layer(s) within technology resource(s) in the radio access network 520, convey the various packetized flows of data streams received through PS gateway node(s) 518. It is to be noted that for technology resource(s) that rely primarily on CS communication, server node(s) can deliver traffic without reliance on PS gateway node(s) 518; for example, server node(s) can embody at least in part a mobile switching center. As an example, in a 3GPP UMTS network, serving node(s) 516 can be embodied in serving GPRS support node(s) (SGSN).

For radio technologies that exploit packetized communication, server(s) 514 in mobile network platform 510 can execute numerous applications that can generate multiple disparate packetized data streams or flows, and manage (e.g., schedule, queue, format . . . ) such flows. Such application(s) can comprise add-on features to standard services (for example, provisioning, billing, customer support . . . ) provided by mobile network platform 510. Data streams (e.g., content(s) that are part of a voice call or data session) can be conveyed to PS gateway node(s) 518 for authorization/authentication and initiation of a data session, and to serving node(s) 516 for communication thereafter. In addition to application server, server(s) 514 can comprise utility server(s), a utility server can comprise a provisioning server, an operations and maintenance server, a security server that can implement at least in part a certificate authority and firewalls as well as other security mechanisms, and the like. In an aspect, security server(s) secure communication served through mobile network platform 510 to ensure network's operation and data integrity in addition to authorization and authentication procedures that CS gateway node(s) 512 and PS gateway node(s) 518 can enact. Moreover, provisioning server(s) can provision services from external network(s) like networks operated by a disparate service provider; for instance, WAN 550 or Global Positioning System (GPS) network(s) (not shown). Provisioning server(s) can also provision coverage through networks associated to mobile network platform 510 (e.g., deployed and operated by the same service provider), such as the distributed antennas networks shown in FIG. 1(s) that enhance wireless service coverage by providing more network coverage.

It is to be noted that server(s) 514 can comprise one or more processors configured to confer at least in part the functionality of mobile network platform 510. To that end, the one or more processor can execute code instructions stored in memory 530, for example. It is should be appreciated that server(s) 514 can comprise a content manager, which operates in substantially the same manner as described hereinbefore.

In example embodiment 500, memory 530 can store information related to operation of mobile network platform 510. Other operational information can comprise provisioning information of mobile devices served through mobile network platform 510, subscriber databases; application intelligence, pricing schemes, e.g., promotional rates, flat-rate programs, couponing campaigns; technical specification(s) consistent with telecommunication protocols for operation of disparate radio, or wireless, technology layers; and so forth. Memory 530 can also store information from at least one of telephony network(s) 540, WAN 550, SS7 network 560, or enterprise network(s) 570. In an aspect, memory 530 can be, for example, accessed as part of a data store component or as a remotely connected memory store.

In order to provide a context for the various aspects of the disclosed subject matter, FIG. 5, and the following discussion, are intended to provide a brief, general description of a suitable environment in which the various aspects of the disclosed subject matter can be implemented. While the subject matter has been described above in the general context of computer-executable instructions of a computer program that runs on a computer and/or computers, those skilled in the art will recognize that the disclosed subject matter also can be implemented in combination with other program modules. Generally, program modules comprise routines, programs, components, data structures, etc. that perform particular tasks and/or implement particular abstract data types.

Figure 6:
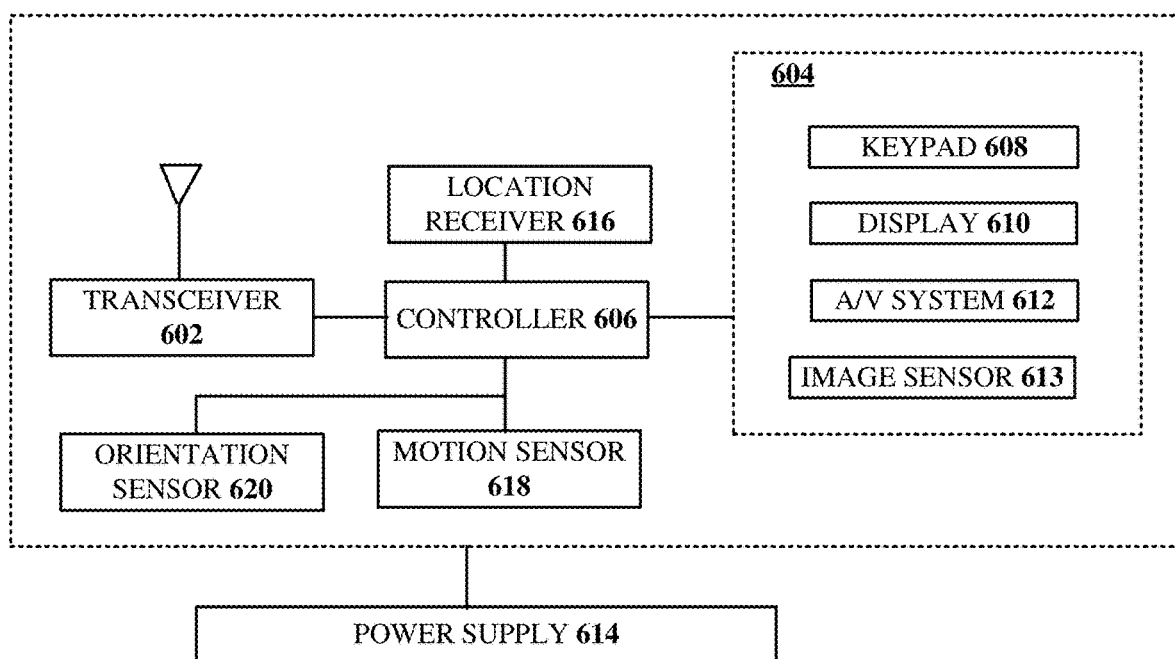
FIG. 6 is a block diagram of an example, non-limiting embodiment of a communication device in accordance with various aspects described herein.

Turning now to FIG. 6, an illustrative embodiment of a communication device 600 is shown. The communication device 600 can serve as an illustrative embodiment of devices such as data terminals 114, mobile devices 124, vehicle 126, display devices 144 or other client devices for communication via either communications network 125. For example, computing device 600 can facilitate in whole or in part providing an immersive environment for a user that includes at least some virtual objects in the immersive environment. The mood of the user may be monitored and objects may be modified to adjust the mood of the user. This can be done, for example, the train the user or modify the user's behavior in certain situations. The computing device 600 can implement the user computer 218, the VR headset 216 or the AR server 220 of FIG. 2B, for example.

The communication device 600 can comprise a wireline and/or wireless transceiver 602 (herein transceiver 602), a user interface (UI) 604, a power supply 614, a location receiver 616, a motion sensor 618, an orientation sensor 620, and a controller 606 for managing operations thereof. The transceiver 602 can support short-range or long-range wireless access technologies such as Bluetooth®, ZigBee®, WiFi, DECT, or cellular communication technologies, just to mention a few (Bluetooth® and ZigBee® are trademarks registered by the Bluetooth® Special Interest Group and the ZigBee® Alliance, respectively). Cellular technologies can include, for example, CDMA-1X, UMTS/HSDPA, GSM/GPRS, TDMA/EDGE, EV/DO, WiMAX, SDR, LTE, as well as other next generation wireless communication technologies as they arise. The transceiver 602 can also be adapted to support circuit-switched wireline access technologies (such as PSTN), packet-switched wireline access technologies (such as TCP/IP, VoIP, etc.), and combinations thereof.

The UI 604 can include a depressible or touch-sensitive keypad 608 with a navigation mechanism such as a roller ball, a joystick, a mouse, or a navigation disk for manipulating operations of the communication device 600. The keypad 608 can be an integral part of a housing assembly of the communication device 600 or an independent device operably coupled thereto by a tethered wireline interface (such as a USB cable) or a wireless interface supporting for example Bluetooth®. The keypad 608 can represent a numeric keypad commonly used by phones, and/or a QWERTY keypad with alphanumeric keys. The UI 604 can further include a display 610 such as monochrome or color LCD (Liquid Crystal Display), OLED (Organic Light Emitting Diode) or other suitable display technology for conveying images to an end user of the communication device 600. In an embodiment where the display 610 is touch-sensitive, a portion or all of the keypad 608 can be presented by way of the display 610 with navigation features.

The display 610 can use touch screen technology to also serve as a user interface for detecting user input. As a touch screen display, the communication device 600 can be adapted to present a user interface having graphical user interface (GUI) elements that can be selected by a user with a touch of a finger. The display 610 can be equipped with capacitive, resistive or other forms of sensing technology to detect how much surface area of a user's finger has been placed on a portion of the touch screen display. This sensing information can be used to control the manipulation of the GUI elements or other functions of the user interface. The display 610 can be an integral part of the housing assembly of the communication device 600 or an independent device communicatively coupled thereto by a tethered wireline interface (such as a cable) or a wireless interface.

The UI 604 can also include an audio system 612 that utilizes audio technology for conveying low volume audio (such as audio heard in proximity of a human ear) and high volume audio (such as speakerphone for hands free operation). The audio system 612 can further include a microphone for receiving audible signals of an end user. The audio system 612 can also be used for voice recognition applications. The UI 604 can further include an image sensor 613 such as a charged coupled device (CCD) camera for capturing still or moving images.

The power supply 614 can utilize common power management technologies such as replaceable and rechargeable batteries, supply regulation technologies, and/or charging system technologies for supplying energy to the components of the communication device 600 to facilitate long-range or short-range portable communications. In other examples, or in combination, the charging system can utilize external power sources such as DC power supplied over a physical interface such as a USB port or other suitable tethering technologies.

The location receiver 616 can utilize location technology such as a global positioning system (GPS) receiver capable of assisted GPS for identifying a location of the communication device 600 based on signals generated by a constellation of GPS satellites, which can be used for facilitating location services such as navigation. The motion sensor 618 can utilize motion sensing technology such as an accelerometer, a gyroscope, or other suitable motion sensing technology to detect motion of the communication device 600 in three-dimensional space. The orientation sensor 620 can utilize orientation sensing technology such as a magnetometer to detect the orientation of the communication device 600 (north, south, west, and east, as well as combined orientations in degrees, minutes, or other suitable orientation metrics).

The communication device 600 can use the transceiver 602 to also determine a proximity to a cellular, WiFi, Bluetooth®, or other wireless access points by sensing techniques such as utilizing a received signal strength indicator (RSSI) and/or signal time of arrival (TOA) or time of flight (TOF) measurements. The controller 606 can utilize computing technologies such as a microprocessor, a digital signal processor (DSP), programmable gate arrays, application specific integrated circuits, and/or a video processor with associated storage memory such as Flash, ROM, RAM, SRAM, DRAM or other storage technologies for executing computer instructions, controlling, and processing data supplied by the aforementioned components of the communication device 600.

Other components not shown in FIG. 6 can be used in one or more embodiments of the subject disclosure. For instance, the communication device 600 can include a slot for adding or removing an identity module such as a Subscriber Identity Module (SIM) card or Universal Integrated Circuit Card (UICC). SIM or UICC cards can be used for identifying subscriber services, executing programs, storing subscriber data, and so on.

The terms "first," "second," "third," and so forth, as used in the claims, unless otherwise clear by context, is for clarity only and doesn't otherwise indicate or imply any order in time. For instance, "a first determination," "a second determination," and "a third determination," does not indicate or imply that the first determination is to be made before the second determination, or vice versa, etc.

In the subject specification, terms such as "store," "storage," "data store," data storage," "database," and substantially any other information storage component relevant to operation and functionality of a component, refer to "memory components," or entities embodied in a "memory" or components comprising the memory. It will be appreciated that the memory components described herein can be either volatile memory or nonvolatile memory, or can comprise both volatile and nonvolatile memory, by way of illustration, and not limitation, volatile memory, non-volatile memory, disk memory, and memory storage. Further, non-volatile memory can be included in read only memory (ROM), programmable ROM (PROM), electrically programmable ROM (EPROM), electrically erasable ROM (EEPROM), or flash memory. Volatile memory can comprise random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

Moreover, it will be noted that the disclosed subject matter can be practiced with other computer system configurations, comprising single-processor or multiprocessor computer systems, mini-computing devices, mainframe computers, as well as personal computers, hand-held computing devices (e.g., PDA, phone, smartphone, watch, tablet computers, netbook computers, etc.), microprocessor-based or programmable consumer or industrial electronics, and the like. The illustrated aspects can also be practiced in distributed computing environments where tasks are performed by remote processing devices that are linked through a communications network; however, some if not all aspects of the subject disclosure can be practiced on stand-alone computers. In a distributed computing environment, program modules can be located in both local and remote memory storage devices.

In one or more embodiments, information regarding use of services can be generated including services being accessed, media consumption history, user preferences, and so forth. This information can be obtained by various methods including user input, detecting types of communications (e.g., video content vs. audio content), analysis of content streams, sampling, and so forth. The generating, obtaining and/or monitoring of this information can be responsive to an authorization provided by the user. In one or more embodiments, an analysis of data can be subject to authorization from user(s) associated with the data, such as an opt-in, an opt-out, acknowledgement requirements, notifications, selective authorization based on types of data, and so forth.

Some of the embodiments described herein can also employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out various embodiments thereof. Moreover, the classifier can be employed to determine a ranking or priority of each cell site of the acquired network. A classifier is a function that maps an input attribute vector, x=(x1, x2, x3, x4, . . . , xn), to a confidence that the input belongs to a class, that is, f(x)=confidence (class). Such classification can employ a probabilistic and/or statistical-based analysis (e.g., factoring into the analysis utilities and costs) to determine or infer an action that a user desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches comprise, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing UE behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to predetermined criteria which of the acquired cell sites will benefit a maximum number of subscribers and/or which of the acquired cell sites will add minimum value to the existing communication network coverage, etc.

As used in some contexts in this application, in some embodiments, the terms "component," "system" and the like are intended to refer to, or comprise, a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, computer-executable instructions, a program, and/or a computer. By way of illustration and not limitation, both an application running on a server and the server can be a component. One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software or firmware that confers at least in part the functionality of the electronic components. While various components have been illustrated as separate components, it will be appreciated that multiple components can be implemented as a single component, or a single component can be implemented as multiple components, without departing from example embodiments.

Further, the various embodiments can be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer program accessible from any computer-readable device or computer-readable storage/ communications media. For example, computer readable storage media can include, but are not limited to, magnetic storage devices (e.g., hard disk, floppy disk, magnetic strips), optical disks (e.g., compact disk (CD), digital versatile disk (DVD)), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Moreover, terms such as "user equipment," "mobile station," "mobile," subscriber station," "access terminal," "terminal," "handset," "mobile device" (and/or terms representing similar terminology) can refer to a wireless device utilized by a subscriber or user of a wireless communication service to receive or convey data, control, voice, video, sound, gaming or substantially any data-stream or signaling-stream. The foregoing terms are utilized interchangeably herein and with reference to the related drawings.

Furthermore, the terms "user," "subscriber," "customer," "consumer" and the like are employed interchangeably throughout, unless context warrants particular distinctions among the terms. It should be appreciated that such terms can refer to human entities or automated components supported through artificial intelligence (e.g., a capacity to make inference based, at least, on complex mathematical formalisms), which can provide simulated vision, sound recognition and so forth.

As employed herein, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of user equipment. A processor can also be implemented as a combination of computing processing units.

As used herein, terms such as "data storage," data storage," "database," and substantially any other information storage component relevant to operation and functionality of a component, refer to "memory components," or entities embodied in a "memory" or components comprising the memory. It will be appreciated that the memory components or computer-readable storage media, described herein can be either volatile memory or nonvolatile memory or can include both volatile and nonvolatile memory.

What has been described above includes mere examples of various embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

In addition, a flow diagram may include a "start" and/or "continue" indication. The "start" and "continue" indications reflect that the steps presented can optionally be incorporated in or otherwise used in conjunction with other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

As may also be used herein, the term(s) "operably coupled to", "coupled to", and/or "coupling" includes direct coupling between items and/or indirect coupling between items via one or more intervening items. Such items and intervening items include, but are not limited to, junctions, communication paths, components, circuit elements, circuits, functional blocks, and/or devices. As an example of indirect coupling, a signal conveyed from a first item to a second item may be modified by one or more intervening items by modifying the form, nature or format of information in a signal, while one or more elements of the information in the signal are nevertheless conveyed in a manner than can be recognized by the second item. In a further example of indirect coupling, an action in a first item can cause a reaction on the second item, as a result of actions and/or reactions in one or more intervening items.

Although specific embodiments have been illustrated and described herein, it should be appreciated that any arrangement which achieves the same or similar purpose may be substituted for the embodiments described or shown by the subject disclosure. The subject disclosure is intended to cover any and all adaptations or variations of various embodiments. Combinations of the above embodiments, and other embodiments not specifically described herein, can be used in the subject disclosure. For instance, one or more features from one or more embodiments can be combined with one or more features of one or more other embodiments. In one or more embodiments, features that are positively recited can also be negatively recited and excluded from the embodiment with or without replacement by another structural and/or functional feature. The steps or functions described with respect to the embodiments of the subject disclosure can be performed in any order. The steps or functions described with respect to the embodiments of the subject disclosure can be performed alone or in combination with other steps or functions of the subject disclosure, as well as from other embodiments or from other steps that have not been described in the subject disclosure. Further, more than or less than all of the features described with respect to an embodiment can also be utilized.

What is claimed is:

1. A device, comprising:
a processing system including a processor; and
a memory that stores executable instructions that, when executed by the processing system, facilitate performance of operations, the operations comprising:
receiving information about a task to be completed by a user;
receiving information about the user;
receiving information about a physical environment of the user;
creating one or more immersion objects, wherein the creating is based on the information about the task, the information about the user and the information about the physical environment;
creating an immersive environment including the one or more immersion objects and at least a portion of the physical environment of the user; and
communicating, to an extended reality (XR) device of the user, information about the immersive environment to create an immersive experience for completion of the task by the user.

2. The device of claim 1, wherein the receiving information about the task to be completed by the user comprises receiving information about training to be completed by the user.

3. The device of claim 1, wherein the receiving information about the task to be completed by the user comprises receiving information about behavioral modification of the user.

4. The device of claim 1, wherein the operations further comprise:
receiving user mood information about a mood of the user during completion of the task by the user;
modifying the immersive environment, wherein the modifying is based on the mood of the user; and
communicating, to the XR device of the user, information about the modified immersive environment.

5. The device of claim 4, wherein the receiving user mood information comprises:
receiving, from one or more sensors associated with the user, biometric information of the user; and
determining from the biometric information if the one or more immersion objects in the immersive environment produces a positive effect on the mood of the user.

6. The device of claim 5, wherein the modifying the immersive environment comprises:
modifying the one or more immersion objects of the immersive environment, wherein the modifying the one or more immersion objects comprises modifying at least one immersion object to produce a positive effect on the mood of the user.

7. The device of claim 1, wherein the receiving information about the user comprises receiving information about a fear of a particular object by the user, and wherein the creating one or more immersion objects comprises creating a virtual object matching the particular object for insertion in the immersive environment with the user.

8. The device of claim 7, wherein the operations further comprise:
progressively exposing the user to the virtual object matching the particular object in the immersive environment.

9. The device of claim 8, wherein the exposing the user to the virtual object comprises:
exposing the user to an image of the virtual object;
receiving, from one or more sensors associated with the user, biometric information of the user;
based on the biometric information, determining a mood of the user; and
increasing exposure of the user to the image of the virtual object based on the determined mood of the user.

10. The device of claim 1, wherein the operations further comprise:
receiving information about training to be completed by the user;
determining a training object associated with the training to be completed by the user; and
adjusting an image of the immersive environment to focus attention of the user on the training object.

11. A non-transitory, machine-readable medium, comprising executable instructions that, when executed by a processing system including a processor, facilitate performance of operations, the operations comprising:
receiving information about training to be completed by a user;
receiving information about a physical environment of the user, including receiving information about a training object associated with the training to be completed by the user;
creating one or more immersion objects, wherein the creating is based on the information about the training to be completed by the user and the information about the physical environment;
creating an immersive environment including the one or more immersion objects and at least a portion of the physical environment of the user;
adjusting an image of the immersive environment to focus attention of the user on the training object; and
communicating, to an extended reality (XR) device of the user, information about the immersive environment to create an immersive experience for completion of the training by the user.

12. The non-transitory, machine-readable medium of claim 11, wherein the adjusting the image of the immersive environment comprises:
blocking or blurring, or a combination of these, objects in the image surrounding the training object.

13. The non-transitory, machine-readable medium of claim 11, wherein the adjusting the image of the immersive environment comprises:
rendering the training object in the image at a first resolution; and
rendering objects in the image surrounding the training object at a second resolution, wherein the second resolution is at a lower resolution to focus the attention of the user on the training object; and
communicating data about first resolution and the second resolution to the XR device of the user, reducing an amount of data for communication of objects in the image rendered at the second resolution.

14. The non-transitory, machine-readable medium of claim 11, wherein the operations further comprise:

during completion of the training by the user, receiving information about a mood of the user;

modifying the immersive environment, wherein the modifying is based on the mood of the user; and communicating, to the XR device of the user, information about the modified immersive environment.

15. The non-transitory, machine-readable medium of claim 14, wherein the receiving information about the mood of the user comprises:

receiving information about activities of the user during completion of the training by the user.

16. A method, comprising:

receiving, by a processing system including a processor, information about a behavioral modification to be completed by a user;

receiving, by the processing system, information about the user;

receiving, by the processing system, information about a physical environment of the user;

creating, by the processing system, one or more immersion objects, wherein the creating is based on the information about the behavioral modification, the information about the user and the information about the physical environment;

creating, by the processing system, an immersive environment including the one or more immersion objects and at least a portion of the physical environment of the user;

communicating, by the processing system, to an extended reality (XR) device of the user, information about the immersive environment to create an immersive experience for completion of the behavioral modification by the user;

receiving, by the processing system, user mood information about a mood of the user during completion of the behavioral modification by the user;

modifying, by the processing system, the immersive environment, wherein the modifying is based on the mood of the user; and communicating, by the processing system, to the XR device of the user, information about the modified immersive environment.

17. The method of claim 16, wherein the receiving user mood information comprises:

receiving, by the processing system, from one or more sensors associated with the user, biometric information of the user; and determining, by the processing system, from the biometric information, if the one or more immersion objects in the immersive environment produces a positive effect on the mood of the user.

18. The method of claim 17, wherein the modifying the immersive environment comprises:

modifying, by the processing system, the one or more immersion objects of the immersive environment to calm the user according to user preferences of the user.

19. The method of claim 16, further comprising:

determining, by the processing system, alternate virtual content for the immersive environment to reduce anxiety in the mood of the user; and providing, by the processing system, the alternate virtual content to the XR device of the user.

20. The method of claim 16, further comprising:

adjusting, by the processing system, an image of the immersive environment to alter the mood of the user.

* * * * *